(12) United States Patent
Hilpert et al.

(10) Patent No.: US 9,388,198 B2
(45) Date of Patent: Jul. 12, 2016

(54) HETEROCYCLIC AMIDE DERIVATIVES AS P2X₇ RECEPTOR ANTAGONISTS

(71) Applicant: ACTELION PHARMACEUTICALS LTD, Allschwil (CH)

(72) Inventors: Kurt Hilpert, Allschwil (CH); Francis Hubler, Allschwil (GB); Dorte Renneberg, Allschwil (CH); Simon Stamm, Allschwil (CH)

(73) Assignee: ACTELION PHARMACEUTICALS LTD., Allschwil (CH)

( * ) Notice: Subject to any disclaimer, the term of this patent is extended or adjusted under 35 U.S.C. 154(b) by 0 days.

(21) Appl. No.: 14/762,717

(22) PCT Filed: Jan. 21, 2014

(86) PCT No.: PCT/IB2014/058434
§ 371 (c)(1),
(2) Date: Jul. 22, 2015

(87) PCT Pub. No.: WO2014/115078
PCT Pub. Date: Jul. 31, 2014

(65) Prior Publication Data
US 2015/0361097 A1 Dec. 17, 2015

(51) Int. Cl.
C07D 277/64 (2006.01)
C07D 277/66 (2006.01)
C07D 277/68 (2006.01)
C07D 277/82 (2006.01)
C07D 513/04 (2006.01)
C07D 277/60 (2006.01)
C07D 417/14 (2006.01)

(52) U.S. Cl.
CPC ............ *C07D 513/04* (2013.01); *C07D 277/60* (2013.01); *C07D 277/64* (2013.01); *C07D 277/66* (2013.01); *C07D 277/68* (2013.01); *C07D 277/82* (2013.01); *C07D 417/14* (2013.01)

(58) Field of Classification Search
USPC .................................................. 548/153, 180
See application file for complete search history.

(56) References Cited

U.S. PATENT DOCUMENTS

| 4,033,977 | A | 7/1977 | Philipp et al. |
| 2002/0156287 | A1* | 10/2002 | Rudolph ............... C07D 277/32 548/150 |
| 2007/0281939 | A1 | 12/2007 | Dombrowski et al. |
| 2012/0157494 | A1 | 6/2012 | Harris, III et al. |

FOREIGN PATENT DOCUMENTS

| EP | 2243772 | 10/2010 |
| WO | WO 00/61569 | 10/2000 |
| WO | WO 01/42194 | 6/2001 |
| WO | WO 01/44170 | 6/2001 |
| WO | WO 01/94338 | 12/2001 |
| WO | WO 03/041707 | 5/2003 |
| WO | WO 03/042190 | 5/2003 |
| WO | WO 03/042191 | 5/2003 |
| WO | WO 03/080579 | 10/2003 |
| WO | WO 2004/058270 | 7/2004 |
| WO | WO 2004/058731 | 7/2004 |
| WO | WO 2004/074224 | 9/2004 |
| WO | WO 2004/099146 | 11/2004 |
| WO | WO 2004/106305 | 12/2004 |
| WO | WO 2005/009968 | 2/2005 |
| WO | WO 2005/111003 | 11/2005 |
| WO | WO 2006/025783 | 3/2006 |
| WO | WO 2006/059945 | 6/2006 |
| WO | WO 2006/080884 | 8/2006 |
| WO | WO 2006/102610 | 9/2006 |
| WO | WO 2007/055374 | 5/2007 |
| WO | WO 2007/109154 | 9/2007 |
| WO | WO 2007/109160 | 9/2007 |
| WO | WO 2007/109172 | 9/2007 |
| WO | WO 2007/109182 | 9/2007 |
| WO | WO 2007/109192 | 9/2007 |
| WO | WO 2007/109201 | 9/2007 |
| WO | WO 2007/141267 | 12/2007 |
| WO | WO 2007/141269 | 12/2007 |
| WO | WO 2008/003697 | 1/2008 |
| WO | WO 2008/066789 | 6/2008 |
| WO | WO 2008/094473 | 8/2008 |
| WO | WO 2008/112205 | 9/2008 |
| WO | WO 2008/114002 | 9/2008 |
| WO | WO 2008/116814 | 10/2008 |

(Continued)

OTHER PUBLICATIONS

Golub et al., Science, vol. 286, Oct. 15, 1999, pp. 531-537.*

(Continued)

*Primary Examiner* — Laura L. Stockton
(74) *Attorney, Agent, or Firm* — Hoxie & Associates LLC

(57) ABSTRACT

The invention relates to heterocyclic amide derivatives of formula (I),

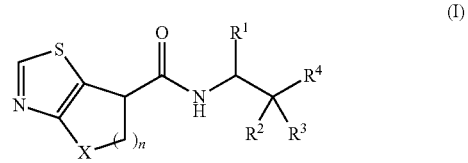

wherein $R^1$, $R^2$, $R^3$, $R^4$, n and X are as defined in the description, their preparation and their use as pharmaceutically active compounds.

17 Claims, No Drawings

(56) References Cited

FOREIGN PATENT DOCUMENTS

| WO | WO 2008/116845 | 10/2008 |
|---|---|---|
| WO | WO 2008/119685 | 10/2008 |
| WO | WO 2008/119825 | 10/2008 |
| WO | WO 2008/124153 | 10/2008 |
| WO | WO 2008/125600 | 10/2008 |
| WO | WO 2008/138876 | 11/2008 |
| WO | WO 2009/012482 | 1/2009 |
| WO | WO 2009/023623 | 2/2009 |
| WO | WO 2009/070116 | 6/2009 |
| WO | WO 2009/074518 | 6/2009 |
| WO | WO 2009/074519 | 6/2009 |
| WO | WO 2009/077362 | 6/2009 |
| WO | WO 2009/077559 | 6/2009 |
| WO | WO 2009/108551 | 9/2009 |
| WO | WO 2009/118175 | 10/2009 |
| WO | WO 2009/132000 | 10/2009 |
| WO | WO 2010/118921 | 10/2010 |
| WO | WO 2011/054947 | 5/2011 |
| WO | WO 2012/114268 | 8/2012 |
| WO | WO 2012/163792 | 12/2012 |
| WO | WO 2013/014587 | 1/2013 |
| WO | WO 2013/108227 | 7/2013 |
| WO | WO 2014/057078 | 4/2014 |
| WO | WO 2014/057080 | 4/2014 |
| WO | WO 2014/091415 | 6/2014 |
| WO | WO 2014/097140 | 6/2014 |
| WO | WO 2014/115072 | 7/2014 |

OTHER PUBLICATIONS

Abberley, et al. "Identification of 2-oxo-n-(phenylmethyl)-4-imidazolidinecarboxamide antagonists of the P2X7 receptor" Bioorganic & Medicinal Chemistry Letters, vol. 20, (Sep. 2010) pp. 6370-6374.

Abdi, et al. "Discovery and structure-activity relationships of a series of pyroglutamic acid amide antagonists of the P2X7 receptor" Bioorganic & Medicinal Chemistry Letters, vol. 20, (Jul. 2010) pp. 5080-5084.

Arbeloa, et al. "P2X7 receptor blockade prevents ATP excitotoxicity in neurons and reduces brain damage after ischemia" Neurobiol Dis vol. 45, No. 3 (2012) pp. 954-961.

Badarau, et. al. "Synthesis of 3-Amino-8-azachromans and 3-Amino-7-azabenzofurans via Inverse Electron Demand Diels-Alder Reaction" Eur. J. Org. Chem., vol. 20 (2009) pp. 3619-3627.

Bartlett, "The P2X7 Receptor Channel: Recent Developments and the Use of P2X7 Antagonists in Models of Disease" Pharmacol. Rev., vol. 66 (Jul. 2014) pp. 638-675.

Chambers, et al. "Synthesis and structure-activity relationships of a series of (1H-pyrazol-4-yl)a-cetamide antangonists of the P2X7 recepter" Bioorganic & Medicinal Chemistry Letters, vol. 20 (Mar. 2010) pp. 3161-3164.

Chen, et al. "Discovery of 2-chloro-n-((4,4-difluoro-1-hdroxycyclohexyl)methyl)-5-(5-fluoropyrimidin-2-yl)benzamide as a potent and CNS penetrable P2X7 receptor antagonist" Bioorganic & Medicinal Chemistry Letters, vol. 20, (Mar. 2010) pp. 3107-3111.

Chessell, et al. "Disruption of the P2X7 purinoceptor gene abolishes chronic inflammatory and neuropathic pain" Pain, vol. 114 (Jan. 2005) pp. 386-396.

Damia, "Contemporary pre-clinical development of anticancer agents—What are the optimal preclinical models?" European Journal of Cancer, vol. 45 (2009) pp. 2768-2781.

Dell' Antonio, et al. "Antinociceptive effect of a new P(2Z)/P2X7 antagonist, oxidized ATP, in arthritic rats" Neurosci Lett., vol. 327, No. 2 (2002) pp. 87-90.

D'Onofrio, "Advances in the identification of g-secretase inhibitors for the treatment of Alzheimer's disease" Expert Opinion on Drug Discovery, vol. 7 (2012) pp. 20-37.

Degraffenreid, et al. "An Efficient and Scalable One-Pot Double Michael Addition-Dieckmann Condensation for the Synthesis of 4,4-Disubstituted Cyclohexane β-keto Esters" J. Org. Chem., vol. 72, No. 19 (2007) pp. 7455-7458.

Deuchars, et al. "Neuronal P2x7 Receptors Are Targeted to Presynaptic Terminals in the Central and Peripheral Nervous Systems" The Journal of Neuroscience, vol. 21, No. 18 (Sep. 2001) pp. 7143-7152.

Duplantier, et al. "Optimization of the Physicochemical and Pharmacokinetic Attributes in a 6-azauracil Series of P2X7 Receptor Antagonists Leading to the Discovery of the Clinical Candidate ce-224,535" Bioorganic & Medicinal Chemistry Letters, vol. 21 (Apr. 2011) pp. 3708-3711.

Eltom, et al., "P2X7 receptor and caspase 1 activation are central to airway inflammation observed after exposure to tobacco smoke" PLoS One, vol. 6, No. 9 (2011) e24097.

Engel, et al. "P2X7 receptor in epilepsy; role in pathophysiology and potential targeting for seizure control" Int J Physiol Pathophysiol Pharmacol, vol. 4, No. 4 (2012) pp. 174-187.

Eser, et al. "Safety and Efficacy of an Oral Inhibitor of the Purinergic Receptor P2X7 in Adult Patients with Moderately to Severely Active Crohn's Disease: A Randomized Placebo-controlled, Double-blind, Phase IIa Study" Inflamm Bowel Dis. vol. 0, No. 0 (Mar. 2015).

Ferrari, et al. "ATP-Mediated Cytotoxicity in Microglial Cells" Neuropharmacology, vol. 36, No. 9 (Jul. 1997) pp. 1295-1301.

Furber, et al. "Discovery of Potent and Selective Adamantane-Based Small-Molecule P2X7 receptor Antagonists/Interleukin-1β Inhibitors" Journal of Medicinal Chemistry, vol. 50 (Oct. 2007) pp. 5882-5885.

Gandelman, et al. "Extracellular ATP and the P2X7 receptor in astrocyte-mediated motor neuron death: implications for amyotrophic lateral sclerosis." J Neuroinflammation, vol. 7, No. 33 (2010), 31 pages.

Gulbransen, et al. "Activation of neuronal P2X7 receptor-pannexin-1 mediates death of enteric neurons during colitis" Nat Med, vol. 18 No. 4 (2012) pp. 600-604.

Gould, "Salt selection for basic drugs" International Journal of Pharmaceutics, vol. 33 (May 1986) pp. 201-217.

Greene, et al. "Protective Groups in Organic Synthesis" Wiley Interscience (1999).

Greenwood-Van Meerveld, "Animal models of gastrointestinal and liver diseases. Animal models of visceral pain: pathophysiology, translational relevance, and challenges" Am. J. Physiol. Gastrointest Liver Physiol., vol. 308 (2015) pp. G885-G903.

Guile, et al. "Antagonists of the P2X7 Receptor. From Lead Identification to Drug Development" Journal of Medicinal Chemistry, vol. 52, No. 10 (May 2009) pp. 3123-3141.

Honore, et al. "A-740003 [N-(1-{[(cyanoimino)(5-quinolinylamino) methyl]amino}-2,2-dimethylpropyl)-2-(3,4-dimethoxyphenyl)acetamide], a novel and selective P2X7 receptor antagonist, dose-dependently reduces neuropathic pain in the rat" J Pharmacol Exp Ther, vol. 319, No. 3 (2006) pp. 1376-1385.

Hook, "Neuroproteases in Peptide Neurotransmission and Neurodegenerative Diseases Applications to Drug Discovery Research" Biodrugs, vol. 20 (2006) pp. 105-119.

Hutchison, et al. "Stereoselective Synthesis of a Conformationally Defined Cyclohexyl Carnitine Analogue That Binds CPT-1 with High Affinity" Bioorganic & Medicinal Chemistry, vol. 7 (Dec. 1999) pp. 1505-1511.

Jhee, et al., "B-amyloid therapies in Alzheimer's disease" Expert Opinion on Ivestigational Drugs, vol. 10 (2001) pp. 593-605.

Johnson, et al., "Relationships between drug activity in NCI preclinical in vitro and in vivo models and early clinical trials" British Journal of Cancer, vol. 84 (2001) pp. 1424-1431.

Julien, "Transgenic mouse models of amyotrophic lateral sclerosis" Biochimica et Biophysica Acta 1762 (2006) pp. 1013-1024.

Keating, et al. (2011). "P2X7 receptor-dependent intestinal afferent hypersensitivity in a mouse model of postinfectious irritable bowel syndrome." J Immunol vol. 187, No. 3 (2011) pp. 1467-1474.

Kitamura, et al. "Powerful Chiral Phase-Transfer Catalysts for the Asymmetic Synthesis of α-Akyl and α,α-Dialkyl-α-amino Acids" Angewandte Chemie, vol. 44 (2005) pp. 1549-1551.

Lang, et al. "Oxidized ATP inhibits T-cell-mediated autoimmunity" Eur J Immunol., vol. 40, No. 9 (2010) pp. 2401-2408.

Le Bars, et al., "Animal Models of Nociception" Pharmacological Reviews, vol. 53, (2001) pp. 597-652.

(56) References Cited

OTHER PUBLICATIONS

Letavic, et al. "Synthesis and Pharmacological Characterization of Two Novel, Brain Penetrating P2X7 Antagonists" ACS Medicinal Chemistry Letters, vol. 4 (Mar. 2013) pp. 419-422.

Lovey, et al. "Isobenzofurans as Conformationally Constrained Miconazole Analogues with Improved Antifungal Potency" Journal of Medicinal Chemistry, vol. 35, No. 22 (1992) pp. 4221-4229.

Madsen-Duggan, et al. "Dihyrdo-pyrano[2,3-b] pyridines and tetrahydro-1,8-naphthyridines as CB1 receptor inverse agonists: Synthesis, SAR and biological evaluation" Bioorganic & Medicinal Chemistry Letters, vol. 20 (Apr. 2010) pp. 3750-3754.

Marcillo, "A reassessment of P2X7 receptor inhibition as a neuroprotective strategy in rat models of contusion injury" Experimental Neurology, vol. 233 (2012) pp. 687-692.

Mezzaroma, et al. "The inflammasome promotes adverse cardiac remodeling following acute myocardial infarction in the mouse" Proc Natl Acad Sci U S A, vol. 108, No. 49 (2011) pp. 19725-19730.

Morita, et al. "Furopyridines. VI. Preparation and Reactions of 2- and 3- Subsituted Furo [2,3-b] pyridines" J. Heterocyclic Chem., vol. 23 (1986) pp. 1465-1469.

Muller, et al. "A potential role for P2X7R in allergic airway inflammation in mice and humans" Am J Respir Cell Mol Biol vol. 44, No. 4 (2011) pp. 456-464.

North, "Molecular Physiology of P2X Receptors" Physiology Review, vol. 82 (Oct. 2002) pp. 1013-1067.

Ocana, "Preclinical development of molecular targeted agents for cancer" Nat. Rev. Clin. Oncol.vol. 8 (2011) pp. 200-209.

Online "DPT-Submission of Pure Compounds for Testing in the NCI Screen" and "NCI 60 Cell Line Screening On-Line Submission Flow Chart" http://dtp.nci.nih.gov/docs/misc/common_files/submit_compounds.html pp. 1-2, Apr. 9, 2015.

Pastore, et al. "Stimulation of purinergic receptors modulates chemokine expression in human keratinocytes" J Invest Dermatol, vol. 127, No. 3 (2007) pp. 660-667.

Peng, et al. "Systemic administration of an antagonist of the ATP-sensitive receptor P2X7 improves recovery after spinal cord injury" Proc Natl Acad Sci U S A, vol. 106, No. 30 (2009) pp. 12489-12493.

Reid, "Epilepsy, energy deficiency and new therapeutic approaches including diet" Pharmacology & Therapeutics, vol. 144 (2014) pp. 192-201.

Remington, The Science and Practice of Pharmacy, 21$^{st}$ Edition (2005) Table of Contents.

Sanz, et al. "Activation of microglia by amyloid {beta} requires P2X7 receptor expression." J Immunol, vol. 182, No. 7 (2009) pp. 4378-4385.

Sharma, "Cell line-based platforms to evaluate the therapeutic efficacy of candidate anticancer agents" Nature Reviews Cancer, vol. 10 (Apr. 2010) pp. 241-253.

Simone, "Oncology: Introduction" Cecil Textbook of Medicine, 20$^{th}$ Edition, vol. 1 (1996) pp. 1004-1010.

Solle, et al. "Mechanisms of Signal Transduction: Altered Cytokine Production in Mice Lacking P2X7 receptors" The Journal of Biological Chemistry, vol. 276, No. 1 (Jan. 2001) pp. 125-132.

Sperlagh, et al. "Involvement of P2X7 Receptors in the regulation of neurotransmitter release in the rat hippocampus" Journal of Neurochemistry, vol. 81 (2002) pp. 1196-1211.

Sperlagh, "P2X7 receptor: and emerging target in central nervous system diseases" Trends in Pharmacological Sciences, vol. 35, No. 10 (Oct. 2014) pp. 537-547.

Stock, "Efficacy and Safety of CE-4224,535, an Antagonist of P2X7 Receptor, in Treatment of Patients with Rheumatoid Arthritis Inadequately Controlled by Methotrexate" The Journal of Rheumatology, vol. 39, No. 4 (2012) pp. 720-727.

Subramanyam, et al. "Discovery, Synthesis and SAR of azinyl- and azolylbenzamides Antagonists of the P2X7 receptor" Bioorganic & Medicinal Chemisty Letters, vol. 21 (2011) pp. 5475-5479.

Surprenant, et al. "The Cytolytic P2Z Receptor for Extracellular ATP Identified as a P2X Receptor (P2X7)" Science, vol. 272, No. 5262 ( May 1996) pp. 735-738.

Taylor, et al. "P2X7 deficiency attenuates renal injury in experimental glomerulonephritis" J Am Soc Nephrol vol. 20, No. 6 (2009) pp. 1275-1281.

Velcicky, et al. "Palladium-Catalyzed Cyanomethylation of Aryl Halides through Domino Suzuki Coupling-Isoxazole Fragmentation" Journal of the American Chemical Society, vol. 133 (Apr. 2011) pp. 6948-6951.

Virginio, et al. "Kinetics of cell lysis, dye uptake and permeability changes in cells expressing the rat P2X7 receptor" Journal of physiology, vol. 519.2 (May 1999) pp. 335-346.

Wang, et al. "Palladium-Catalyzed One-Pot Synthesis of 2-Alkyl-2-arylcyanoacetates" Journal Organic Chemistry, vol. 73, No. 4, (2008) pp. 1643-1645.

Wesselius, et al. "Role of purinergic receptor polymorphisms in human bone" Front Biosci (Landmark Ed) vol. 16 (2011) pp. 2572-2585.

Wiley, et al. "Transduction Mechanisms of P2Z Purinoceptors" Ciba Foundation Symposium, vol. 198 (1996) pp. 149-160 and 160-165.

Yu, et al. "Cellular localization of P2X7 receptor mRNA in the rat brain" Brain Research, vol. 1194 (2008) pp. 45-55.

Yuzwa, "O-GlcNAc and neurodegeneration: biochemical mechanisms and potential roles in Alzheimer's disease and beyond" Chem. Soc. Rev., vol. 43 (2014) 6839-6858.

\* cited by examiner

HETEROCYCLIC AMIDE DERIVATIVES AS P2X₇ RECEPTOR ANTAGONISTS

CROSS REFERENCE TO RELATED APPLICATIONS

This application is filed under 35 U.S.C. 371 as a U.S. National Phase Application of International Application No. PCT/IB2014/058434 filed Jan. 21, 2014, which claims benefit of European Application No. 13152273.2 filed Jan. 22, 2013.

The present invention relates to heterocyclic amide derivatives of formula (I) and their use as pharmaceuticals. The invention also concerns related aspects including processes for the preparation of the compounds, pharmaceutical compositions containing one or more compounds of formula (I), and especially their use as P2X$_7$ receptor antagonists.

The P2X$_7$ receptors (P2RX7) belong to the family of P2X ionotropic receptors that are activated by extracellular nucleotides, in particular adenosine triphosphate (ATP). P2RX7 is distinguished from other P2X family members by the high concentrations (mM range) of ATP required to activate it and its ability to form a large pore upon prolonged or repeated stimulation (North, R. A., Physiol. Rev. 2002, 82(4), 1013-67; Surprenant, A., Rassendren, F. et al., Science 1996, 272(5262), 735-8; Virginio, C., MacKenzie, A. et al., J. Physiol., 1999, 519, 335-46). P2RX7 is present on many cell types, especially ones known to be involved in inflammatory and immune processes. This is reflected within both the periphery and the CNS as Lipopolysaccharide S (LPS) priming of monocytes and microglia followed by ATP stimulation has been shown to lead to the local release and processing of IL1β and other family members including IL18 through a P2RX7 mediated mechanism. Indeed mice lacking the P2X7 receptor are unable to release IL1β, following LPS priming and ATP stimulation providing further evidence of its role in this pathway (Solle, M., Labasi, J. et al., J. Biol. Chem., 2001, 276(1), 125-32). In addition L-selectin shedding from monocytes, macrophages and lymphocytes, degranulation in mast cells and apoptosis in lymphocytes are all associated with P2RX7 stimulation. P2RX7 is also expressed on epithelial and endothelial cells (Ferrari, D., Chiozzi, P. et al., Neuropharmacology 1997, 36(9), 1295-301; Wiley, J. S., Chen, J. R. et al., Ciba Found Symp. 1996, 198, 149-60 and 160-5; North, R. A., Physiol. Rev. 2002, 82(4), 1013-67). In addition to its role in the periphery it may have an important function in neurotransmission within the CNS through its activation on postsynaptic and/or presynaptic central and peripheral neurons and glia (Deuchars, S. A., Atkinson, L. et al., J. Neurosci. 2001, 21(18), 7143-52; Sperlagh, B., Kofalvi, A. et al., J. Neurochem. 2002, 81(6), 1196-211). Recent data that has emerged using in situ hybridization demonstrated that P2X7 receptor mRNA was widely distributed throughout the rat brain. Specifically, among the areas of high P2X7 mRNA expression noted were the piriform cortex, hippocampus, pontine nuclei and the anterior horn of the spinal cord (Yu, Y., Ugawa, S. et al., Brain. Res. 2008, 1194, 45-55). Hence there is therapeutic rationale for the use of P2X7 ion channel blockers in the treatment of a variety of disease states. These include but are not limited to diseases associated with the central nervous system such as stroke or injury and diseases associated with neuro-degeneration and neuroinflammation such as Alzheimer's disease, Huntington's disease, epilepsy, Amyotrophic lateral sclerosis, acute spinal cord injury additionally to meningitis, sleep disorders, mood and anxiety disorders as well as chronic and neuropathic and inflammatory pain. Furthermore, peripheral inflammatory disorders and autoimmune diseases including but not limited to rheumatoid arthritis, osteoarthritis, psoriasis, allergic dermatitis, asthma, chronic obstructive pulmonary disease, airways hyper-responsiveness, septic shock, bronchitis, glomerulonephritis, irritable bowel disease, skin injury, lung emphysema, Limb girdle dystrophy type 2B, fibrosis, Syndrome of synovitis Acne Pustulosis, atherosclerosis, burn injury, spinal cord injury, Hyperostosis Osteitis, Crohn's disease, ulcerative colitis, growth and metastases of malignant cells, myoblastic leukaemia, diabetes, trauma, meningitis, osteoporosis, burn injury, ischemic heart disease, and varicose veins and trauma, are all examples where the involvement of P2X7 channels has been implicated. In addition a recent report suggests a link between P2RX7 and chronic, inflammatory and neuropathic pain (Chessell, I. P., Hatcher, J. P. et al., Pain, 2005, 114(3), 386-96). Overall, these findings indicate a role for the P2X7 receptor in the process of neuronal synaptic transmission and therefore a potential role for P2X7 antagonists as novel therapeutic tools to treat neuropathic pain.

In view of the above observations, there is significant requirement for P2X7 antagonists that can be efficiently used in treating neuropathic pain, chronic inflammatory pain, inflammation, and neurodegenerative conditions.

Different carboxamide derivatives, which are also P2X$_7$ receptor antagonists, have been for instance disclosed in WO 2008/066789 (imidazo[1,2-a]pyridine derivatives), WO 2008/124153 (pyrazolo[1,5-a]pyridine derivatives), WO 2009/023623 (1H-pyrrolo[2,3-b]pyridine and indole derivatives), WO 2009/108551 (indole derivatives) and WO 2009/132000 (quinoline and isoquinoline derivatives). Other P2X$_7$ receptor antagonists with a heterocyclic amide structure have been disclosed in WO 2013/108227.

Various embodiments of the invention are presented hereafter:

1) The present invention relates to heterocyclic amide derivatives of formula (I),

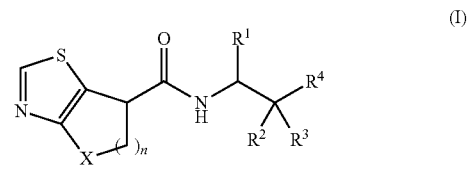

(I)

wherein
n represents 1, 2 or 3;
X represents —O— or —CH$_2$—;
R$^1$ represents hydrogen, (C$_1$-C$_2$)alkyl or hydroxy-(C$_1$-C$_2$)alkyl;
R$^2$ represents hydrogen and R$^3$ represents heterocyclyl; or R$^2$ and R$^3$ form, together with the carbon atom to which they are attached, a 5- to 7-membered saturated carbocyclic ring which is unsubstituted or mono- or di-substituted with fluoro; and
R$^4$ represents hydrogen or heteroaryl which is unsubstituted or mono- or di-substituted with (C$_1$-C$_4$)alkyl, (C$_1$-C$_3$)fluoroalkyl or halogen;
and to the salts (in particular pharmaceutically acceptable salts) of such compounds.

The compounds of formula (I) according to embodiment 1) may contain one or more stereogenic or asymmetric centers, such as one or more asymmetric carbon atoms. Substituents at a double bond may be present in the (Z)- or (E)-configuration unless indicated otherwise. The compounds of formula (I) may thus be present as mixtures of stereoisomers or preferably as pure stereoisomers. Mixtures of stereoisomers may be separated in a manner known to a person skilled in the art.

Definitions provided herein are intended to apply uniformly to the compounds of formulae (I), ($I_{St1}$), ($I_{St2}$) and ($I_{St3}$), as defined in any one of embodiments 1) to 22), and, mutatis mutandis, throughout the description and the claims unless an otherwise expressly set out definition provides a broader or narrower definition. It is well understood that a definition or preferred definition of a term defines and may replace the respective term independently of (and in combination with) any definition or preferred definition of any or all other terms as defined herein.

The term "alkyl", used alone or in combination, refers to a straight or branched chain alkyl group containing one to four carbon atoms. The term "($C_x$-$C_y$)alkyl" (x and y each being an integer), refers to an alkyl group as defined before containing x to y carbon atoms. For example a ($C_1$-$C_4$)alkyl group contains from one to four carbon atoms. Representative examples of alkyl groups include methyl, ethyl, n-propyl, iso-propyl, n-butyl, iso-butyl, sec.-butyl and tert.-butyl.

In case "$R^1$" represents "($C_1$-$C_2$)alkyl" the term means ($C_1$-$C_2$)alkyl groups as defined above. Examples of said groups are methyl and ethyl. Preferred is methyl.

In case "($C_1$-$C_4$)alkyl" is a substituent to a heteroaryl group, the term "($C_1$-$C_4$)alkyl" means ($C_1$-$C_4$)alkyl groups as defined above. Examples of said groups are methyl, ethyl, n-propyl, iso-propyl, n-butyl, iso-butyl, sec.-butyl and tert.-butyl. Preferred is methyl.

The term "hydroxy-($C_x$-$C_y$)alkyl" (x and y each being an integer), used alone or in combination, refers to an alkyl group as defined before containing x to y carbon atoms in which one hydrogen atom has been replaced with hydroxy. For example a hydroxy-($C_1$-$C_2$)alkyl group contains one or two carbon atoms in which one hydrogen atom has been replaced with hydroxy. Examples of said groups are hydroxy-methyl and hydroxy-ethyl.

In case "$R^1$" represents "hydroxy-($C_1$-$C_2$)alkyl" the term means hydroxy-($C_1$-$C_2$)alkyl groups as defined above. Representative examples of said groups are hydroxy-methyl, 1-hydroxy-ethyl and 2-hydroxy-ethyl. Preferred is hydroxy-methyl.

The term "5- to 7-membered saturated carbocyclic ring", used alone or in combination, refers to a saturated monocyclic ring containing 5, 6 or 7 carbon atoms. Preferred are saturated monocyclic rings containing 6 or 7 carbon atoms; and most preferred is a saturated monocyclic ring containing 6 carbon atoms. Examples of said rings are cyclopentyl, cyclohexyl and cycloheptyl. Most preferred is cyclohexyl.

The term "($C_x$-$C_y$)fluoroalkyl" (x and y each being an integer) refers to an alkyl group as defined before containing x to y carbon atoms in which one or more (and possibly all) hydrogen atoms have been replaced with fluoro. For example a ($C_1$-$C_3$)fluoroalkyl group contains from one to three carbon atoms in which one to seven hydrogen atoms have been replaced with fluoro.

In case "($C_1$-$C_3$)fluoroalkyl" is a substituent to a heteroaryl group, the term "($C_1$-$C_3$)fluoroalkyl" means ($C_1$-$C_3$)fluoroalkyl groups as defined above. Representative examples of said groups are difluoromethyl, trifluoromethyl, 2,2-difluoroethyl and 2,2,2-trifluoroethyl. Preferred is trifluoromethyl.

The term halogen means fluoro, chloro or bromo.

In case "halogen" is a substituent to a heteroaryl group, the term "halogen" means fluoro, chloro or bromo; and preferably chloro.

The term "heterocyclyl", used alone or in combination, refers to a saturated monocyclic moiety of 5 to 7 ring members containing a nitrogen atom and optionally one additional heteroatom selected from nitrogen, oxygen and sulfur. Preferred is a 6-membered heterocyclyl group. The heterocyclyl group is preferably attached to the rest of the molecule via a nitrogen atom. Representative examples of such heterocyclyl groups are pyrrolidinyl, piperidinyl, piperazinyl, morpholinyl, thiomorpholinyl, azepanyl, 1,4-oxazepanyl and 1,4-thiazepanyl. Preferred examples are piperidinyl (notably piperidin-1-yl) and morpholinyl (notably morpholin-4-yl). The heterocyclyl group is unsubstituted or mono- or di-substituted with fluoro. Most preferred examples of unsubstituted or mono- or di-substituted heterocyclyl groups are 4,4-difluoro-piperidin-1-yl and morpholin-4-yl.

The term "6-membered heterocyclyl", used alone or in combination, refers to a saturated monocyclic moiety of 6 ring members containing one nitrogen atom and optionally one oxygen atom. The 6-membered heterocyclyl group is preferably attached to the rest of the molecule via the nitrogen atom. Representative examples of such heterocyclyl groups are piperidinyl and morpholinyl. Preferred examples are piperidin-1-yl and morpholin-4-yl. The 6-membered heterocyclyl group is unsubstituted or mono- or di-substituted with fluoro. Most preferred examples of unsubstituted or mono- or di-substituted 6-membered heterocyclyl groups are 4,4-difluoro-piperidin-1-yl and morpholin-4-yl.

The term "heteroaryl", used alone or in combination, means a 5- or 6-membered monocyclic aromatic ring containing 1 or 2 heteroatoms independently selected from oxygen, nitrogen and sulphur. Preferred is a 6-membered heteroaryl group. Examples are furanyl, oxazolyl, isoxazolyl, thienyl, thiazolyl, isothiazolyl, pyrrolyl, imidazolyl, pyrazolyl, pyridyl, pyrimidyl, pyridazinyl and pyrazinyl. Preferred examples are pyridyl (notably pyridin-3-yl) and pyrimidyl (notably pyrimidin-5-yl). The heteroaryl group is unsubstituted or substituted as explicitly defined. Preferred examples of unsubstituted or substituted heteroaryl groups are 2-chloro-pyridin-5-yl, 2-trifluoromethyl-pyridin-5-yl, 2-methyl-pyrimidin-5-yl and 2-trifluoromethyl-pyrimidin-5-yl. Most preferred is 2-chloro-pyridin-5-yl.

The term "6-membered heteroaryl", used alone or in combination, means a 6-membered monocyclic aromatic ring containing 1 or 2 nitrogen atoms. Examples are pyridyl, pyrimidyl, pyridazinyl and pyrazinyl. Preferred examples are pyridyl (notably pyridin-3-yl) and pyrimidyl (notably pyrimidin-5-yl). The 6-membered heteroaryl group is unsubstituted or substituted as explicitly defined. Preferred examples of unsubstituted or substituted heteroaryl groups are 2-chloro-pyridin-5-yl, 2-trifluoromethyl-pyridin-5-yl, 2-methyl-pyrimidin-5-yl and 2-trifluoromethyl-pyrimidin-5-yl. Most preferred is 2-chloro-pyridin-5-yl.

2) A further embodiment of the invention relates to compounds according to embodiment 1), wherein n represents 1, 2 or 3;

X represents —O— or —$CH_2$—;

$R^1$ represents hydrogen, ($C_1$-$C_2$)alkyl or hydroxy-($C_1$-$C_2$)alkyl;

$R^2$ represents hydrogen and $R^3$ represents 6-membered heterocyclyl; or $R^2$ and $R^3$ form, together with the carbon atom to which they are attached, a 6- or 7-membered saturated carbocyclic ring which is unsubstituted or mono- or di-substituted with fluoro; and $R^4$ represents hydrogen or a 6-membered heteroaryl group, which group is unsubstituted or mono- or di-substituted with ($C_1$-$C_4$)alkyl, ($C_1$-$C_3$)fluoroalkyl or halogen;

with the proviso that one of $R^1$ and $R^4$ is different from hydrogen;

and to the salts (in particular pharmaceutically acceptable salts) of such compounds.

3) A further embodiment of the invention relates to compounds according to any one of embodiments 1) or 2), wherein n represents 1 or 2;
X represents —O— or —CH$_2$—;
R$^1$ represents hydrogen, methyl or hydroxy-methyl;
R$^2$ represents hydrogen and R$^3$ represents 6-membered heterocyclyl; or R$^2$ and R$^3$ form, together with the carbon atom to which they are attached, a 6- or 7-membered saturated carbocyclic ring which is unsubstituted or mono- or di-substituted with fluoro; and
R$^4$ represents hydrogen or a 6-membered heteroaryl group, which group is mono-substituted with methyl, trifluoromethyl or chloro;
and to the salts (in particular pharmaceutically acceptable salts) of such compounds.

4) A further embodiment of the invention relates to compounds according to embodiment 1), wherein n represents 1 or 2;
X represents —O— or —CH$_2$—;
R$^1$ represents hydrogen;
R$^2$ represents hydrogen and R$^3$ represents heterocyclyl; or (preferably) R$^2$ and R$^3$ form, together with the carbon atom to which they are attached, a 6- or 7-membered saturated carbocyclic ring which is unsubstituted or mono- or di-substituted with fluoro; and
R$^4$ represents heteroaryl which is unsubstituted or mono- or di-substituted with (C$_1$-C$_4$)alkyl, (C$_1$-C$_3$)fluoroalkyl or halogen;
and to the salts (in particular pharmaceutically acceptable salts) of such compounds.

5) A further embodiment of the invention relates to compounds according to embodiment 1), wherein n represents 1 or 2;
X represents —O— or —CH$_2$—;
R$^1$ represents hydrogen;
R$^2$ represents hydrogen and R$^3$ represents 6-membered heterocyclyl; or R$^2$ and R$^3$ form, together with the carbon atom to which they are attached, a 6-membered saturated carbocyclic ring which is unsubstituted or di-substituted with fluoro; and
R$^4$ represents a 6-membered heteroaryl group, which group is unsubstituted or mono-substituted with methyl, trifluoromethyl or chloro;
and to the salts (in particular pharmaceutically acceptable salts) of such compounds.

6) A further embodiment of the invention relates to compounds according to embodiment 1), wherein n represents 1 or 2;
X represents —O— or —CH$_2$—;
R$^1$ represents hydrogen;
R$^2$ and R$^3$ form, together with the carbon atom to which they are attached, a 6-membered saturated carbocyclic ring which is unsubstituted or di-substituted with fluoro; and
R$^4$ represents a 6-membered heteroaryl group, which group is mono-substituted with chloro;
and to the salts (in particular pharmaceutically acceptable salts) of such compounds.

7) A further embodiment of the invention relates to compounds according to embodiment 1), wherein n represents 1, 2 or 3;
X represents —O— or —CH$_2$—;
R$^1$ represents (C$_1$-C$_2$)alkyl or hydroxy-(C$_1$-C$_2$)alkyl;
R$^2$ and R$^3$ form, together with the carbon atom to which they are attached, a 6- or 7-membered saturated carbocyclic ring which is unsubstituted; and
R$^4$ represents hydrogen;
and to the salts (in particular pharmaceutically acceptable salts) of such compounds.

8) A further embodiment of the invention relates to compounds according to embodiment 1), wherein n represents 1 or 2;
X represents —O— or —CH$_2$—;
R$^1$ represents methyl or hydroxy-methyl;
R$^2$ and R$^3$ form, together with the carbon atom to which they are attached, a 6-membered saturated carbocyclic ring which is unsubstituted; and
R$^4$ represents hydrogen;
and to the salts (in particular pharmaceutically acceptable salts) of such compounds.

9) A further embodiment of the invention relates to compounds according to any one of embodiments 1), 2) or 7), wherein n represents 1 or 2;
and to the salts (in particular pharmaceutically acceptable salts) of such compounds.

10) A further embodiment of the invention relates to compounds according to any one of embodiments 1) to 8), wherein n represents 1;
and to the salts (in particular pharmaceutically acceptable salts) of such compounds.

11) A further embodiment of the invention relates to compounds according to any one of embodiments 1) to 8), wherein n represents 2;
and to the salts (in particular pharmaceutically acceptable salts) of such compounds.

12) A further embodiment of the invention relates to compounds according to any one of embodiments 1) to 11), wherein X represents —O—;
and to the salts (in particular pharmaceutically acceptable salts) of such compounds.

13) A further embodiment of the invention relates to compounds according to any one of embodiments 1) to 11), wherein X represents —CH$_2$—;
and to the salts (in particular pharmaceutically acceptable salts) of such compounds.

14) A further embodiment of the invention relates to compounds according to any one of embodiments 1), 2), 7) or 9) to 13), wherein R$^1$ represents hydroxy-(C$_1$-C$_2$)alkyl;
and to the salts (in particular pharmaceutically acceptable salts) of such compounds.

15) A further embodiment of the invention relates to compounds according to any one of embodiments 1), 4) or 9) to 14), wherein R$^2$ represents hydrogen and R$^3$ represents heterocyclyl;
and to the salts (in particular pharmaceutically acceptable salts) of such compounds.

16) A further embodiment of the invention relates to compounds according to any one of embodiments 1) to 5) or 9) to 14), wherein R$^2$ represents hydrogen and R$^3$ represents 6-membered heterocyclyl;
and to the salts (in particular pharmaceutically acceptable salts) of such compounds.

17) A further embodiment of the invention relates to compounds according to any one of embodiments 1) to 6) or 9) to 14), wherein
R² and R³ form, together with the carbon atom to which they are attached, a 6-membered saturated carbocyclic ring which is unsubstituted or di-substituted with fluoro;
and to the salts (in particular pharmaceutically acceptable salts) of such compounds.

18) A further embodiment of the invention relates to compounds according to any one of embodiments 1) to 5) or 9) to 17), wherein
R⁴ represents a 6-membered heteroaryl group, which group is unsubstituted or mono-substituted with methyl, trifluoromethyl or chloro;
and to the salts (in particular pharmaceutically acceptable salts) of such compounds.

19) A further embodiment of the invention relates to compounds according to any one of embodiments 1) to 18), wherein the stereogenic center at the α-carbon atom of the amide moiety is as depicted in formula ($I_{St1}$)

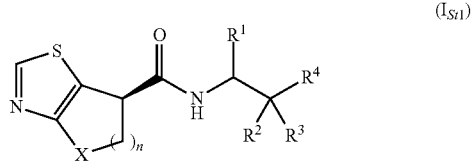

and to the salts (in particular pharmaceutically acceptable salts) of such compounds.

20) A further embodiment of the invention relates to compounds according to any one of embodiments 1) to 18), wherein the stereogenic center at the α-carbon atom of the amide moiety is as depicted in formula ($I_{St2}$)

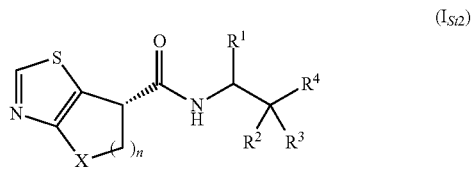

and to the salts (in particular pharmaceutically acceptable salts) of such compounds.

21) A further embodiment of the invention relates to compounds according to any one of embodiments 1) to 20), wherein the stereogenic center at the carbon atom which is attached to R¹ is as depicted in formula ($I_{St3}$)

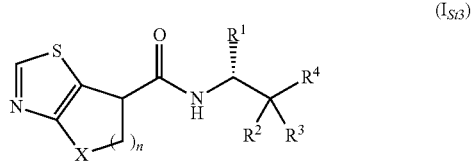

and to the salts (in particular pharmaceutically acceptable salts) of such compounds.

22) Preferred compounds of formula (I) as defined in embodiment 1) are selected from the group consisting of:
N-(1-cycloheptyl-2-hydroxyethyl)-5,6-dihydrofuro[2,3-d]thiazole-6-carboxamide;
N-((1-(6-chloropyridin-3-yl)cyclohexyl)methyl)-5,6-dihydrofuro[2,3-d]thiazole-6-carboxamide;
N-(2-(4,4-difluoropiperidin-1-yl)-2-(2-methylpyrimidin-5-yl)ethyl)-5,6-dihydrofuro[2,3-d]thiazole-6-carboxamide;
N-(2-morpholino-2-(6-(trifluoromethyl)pyridin-3-yl)ethyl)-5,6-dihydrofuro[2,3-d]thiazole-6-carboxamide;
N—((S)-1-cyclohexyl-2-hydroxyethyl)-5,6-dihydro-4H-cyclopenta[d]thiazole-6-carboxamide;
N-(2-(2-methylpyrimidin-5-yl)-2-morpholinoethyl)-5,6-dihydro-4H-cyclopenta[d]thiazole-6-carboxamide;
N-(2-(4,4-difluoropiperidin-1-yl)-2-(2-methylpyrimidin-5-yl)ethyl)-5,6-dihydro-4H-cyclopenta[d]thiazole-6-carboxamide;
N—((S)-1-cyclohexyl-2-hydroxyethyl)-6,7-dihydro-5H-pyrano[2,3-d]thiazole-7-carboxamide;
N-(2-(2-methylpyrimidin-5-yl)-2-morpholinoethyl)-6,7-dihydro-5H-pyrano[2,3-d]thiazole-7-carboxamide;
N-(2-(6-chloropyridin-3-yl)-2-(4,4-difluoropiperidin-1-yl)ethyl)-6,7-dihydro-5H-pyrano[2,3-d]thiazole-7-carboxamide;
N—((R)-1-cyclohexylethyl)-4,5,6,7-tetrahydrobenzo[d]thiazole-7-carboxamide;
N—((S)-1-cyclohexyl-2-hydroxyethyl)-4,5,6,7-tetrahydrobenzo[d]thiazole-7-carboxamide;
N-((1-(6-chloropyridin-3-yl)cyclohexyl)methyl)-4,5,6,7-tetrahydrobenzo[d]thiazole-7-carboxamide;
N-((1-(6-chloropyridin-3-yl)-4,4-difluorocyclohexyl)methyl)-4,5,6,7-tetrahydrobenzo[d]thiazole-7-carboxamide;
N-(2-morpholino-2-(2-(trifluoromethyl)pyrimidin-5-yl)ethyl)-4,5,6,7-tetrahydrobenzo[d]thiazole-7-carboxamide;
N—((S)-1-cyclohexyl-2-hydroxyethyl)-(S)-5,6,7,8-tetrahydro-4H-cyclohepta[d]thiazole-8-carboxamide; and
N—((S)-1-cyclohexyl-2-hydroxyethyl)-(R)-5,6,7,8-tetrahydro-4H-cyclohepta[d]thiazole-8-carboxamide;
or salts (in particular pharmaceutically acceptable salts) of such compounds;

it is to be understood for any of the above listed compounds, that a stereogenic center, which is not specifically assigned, may be in absolute (R)- or absolute (S)-configuration; for example, the stereogenic center at the α-carbon atom of the amide moiety may be in absolute (R)-configuration or absolute (S)-configuration. For example a compound listed as N-((1-(6-chloropyridin-3-yl)cyclohexyl)methyl)-4,5,6,7-tetrahydrobenzo[d]thiazole-7-carboxamide may be N-((1-(6-chloropyridin-3-yl)cyclohexyl)methyl)-(S)-4,5,6,7-tetrahydrobenzo[d]thiazole-7-carboxamide, N-((1-(6-chloropyridin-3-yl)cyclohexyl)methyl)-(R)-4,5,6,7-tetrahydrobenzo[d]thiazole-7-carboxamide or any mixture thereof. Notably, compounds containing more than one stereogenic center may be at each stereogenic center, which is not specifically assigned, in absolute (R)- or absolute (S)-configuration; for example a compound listed as N-(2-morpholino-2-(2-(trifluoromethyl)pyrimidin-5-yl)ethyl)-4,5,6,7-tetrahydrobenzo[d]thiazole-7-carboxamide may be N—((S)-2-morpholino-2-(2-(trifluoromethyl)pyrimidin-5-yl)ethyl)-(S)-4,5,6,7-tetrahydrobenzo[d]thiazole-7-carboxamide, N—((S)-2-morpholino-2-(2-(trifluoromethyl)pyrimidin-5-yl)ethyl)-(R)-4,5,6,7-tetrahydrobenzo[d]thiazole-7-carboxamide, N—((R)-2-morpholino-2-(2-(trifluoromethyl)pyrimidin-5-yl)ethyl)-(S)-4,5,6,7-tetrahydrobenzo[d]thiazole-7-carboxamide, N—((R)-2-morpholino-2-(2-(trifluoromethyl)pyrimidin-5-yl)ethyl)-(R)-4,5,6,7-tetrahydrobenzo[d]thiazole-7-carboxamide or any mixture thereof.

It is well understood that the invention relates to compounds according to embodiment 1); or according to embodiment 1) limited by the features of an embodiment dependent on embodiment 1; or according to embodiment 1) limited by the features of a cascade of dependent embodiments e.g. in the form of "embodiment 3) depending on embodiment 2) depending on embodiment 1)". In case of an embodiment depending on more than one other embodiment, it is understood that each combination is specifically disclosed. Also, in case an embodiment is dependent on more than one other embodiment and one or more of said other embodiments are themselves dependent on one or more further embodiments, it is understood that each combination is specifically disclosed if obtainable with regard to the given dependencies and multiple dependencies. Notably, embodiments resulting from cascades of more than three embodiments depending on each other may be construed under observance of the given dependencies and multiple dependencies and are thus intended to be specifically disclosed. Representative examples of embodiments which are possible based on the dependencies of the embodiments 1) to 22) as disclosed hereinabove and which are therefore intended and herewith specifically disclosed in individualized form are:

1, 2+1, 3+1, 3+2+1, 4+1, 5+1, 6+1, 7+1, 8+1, 9+1, 9+2+1, 9+7+1, 10+1, 10+2+1, 10+3+1, 10+3+2+1, 10+4+1, 10+5+1, 10+6+1, 10+7+1, 10+8+1, 11+1, 11+2+1, 11+3+1, 11+3+2+1, 11+4+1, 11+5+1, 11+6+1, 11+7+1, 11+8+1, 12+1, 12+2+1, 12+3+1, 12+3+2+1, 12+4+1, 12+5+1, 12+6+1, 12+7+1, 12+8+1, 12+9+1, 12+9+2+1, 12+9+7+1, 12+10+1, 12+10+2+1, 12+10+3+1, 12+10+3+2+1, 12+10+4+1, 12+10+5+1, 12+10+6+1, 12+10+7+1, 12+10+8+1, 12+11+1, 12+11+2+1, 12+11+3+1, 12+11+3+2+1, 12+11+4+1, 12+11+5+1, 12+11+6+1, 12+11+7+1, 12+11+8+1, 13+1, 13+2+1, 13+3+1, 13+3+2+1, 13+4+1, 13+5+1, 13+6+1, 13+7+1, 13+8+1, 13+9+1, 13+9+2+1, 13+9+7+1, 13+10+1, 13+10+2+1, 13+10+3+1, 13+10+3+2+1, 13+10+4+1, 13+10+5+1, 13+10+6+1, 13+10+7+1, 13+10+8+1, 13+11+1, 13+11+2+1, 13+11+3+1, 13+11+3+2+1, 13+11+4+1, 13+11+5+1, 13+11+6+1, 13+11+7+1, 13+11+8+1, 14+1, 14+2+1, 14+7+1, 14+9+1, 14+9+2+1, 14+9+7+1, 14+11+1, 14+11+2+1, 14+11+3+1, 14+11+3+2+1, 14+11+4+1, 14+11+5+1, 14+11+6+1, 14+11+7+1, 14+11+8+1, 14+12+1, 14+12+2+1, 14+12+3+1, 14+12+3+2+1, 14+12+4+1, 14+12+5+1, 14+12+6+1, 14+12+7+1, 14+12+8+1, 14+12+9+1, 14+12+9+2+1, 14+12+9+7+1, 14+12+10+1, 14+12+10+2+1, 14+12+10+3+1, 14+12+10+3+2+1, 14+12+10+4+1, 14+12+10+5+1, 14+12+10+6+1, 14+12+10+7+1, 14+12+10+8+1, 14+12+11+1, 14+12+11+2+1, 14+12+11+3+1, 14+12+11+3+2+1, 14+12+11+4+1, 14+12+11+5+1, 14+12+11+6+1, 14+12+11+7+1, 14+12+11+8+1, 14+13+1, 14+13+2+1, 14+13+3+1, 14+13+3+2+1, 14+13+4+1, 14+13+5+1, 14+13+6+1, 14+13+7+1, 14+13+8+1, 14+13+9+1, 14+13+9+2+1, 14+13+9+7+1, 14+13+10+1, 14+13+10+2+1, 14+13+10+3+1, 14+13+10+3+2+1, 14+13+10+4+1, 14+13+10+5+1, 14+13+10+6+1, 14+13+10+7+1, 14+13+10+8+1, 14+13+11+1, 14+13+11+2+1, 14+13+11+3+1, 14+13+11+3+2+1, 14+13+11+4+1, 14+13+11+5+1, 14+13+11+6+1, 14+13+11+7+1, 14+13+11+8+1, 15+1, 15+4+1, 15+9+1, 15+9+2+1, 15+9+7+1, 15+13+1, 15+13+2+1, 15+13+3+1, 15+13+3+2+1, 15+13+4+1, 15+13+5+1, 15+13+6+1, 15+13+7+1, 15+13+8+1, 15+13+9+1, 15+13+9+2+1, 15+13+9+7+1, 15+13+10+1, 15+13+10+2+1, 15+13+10+3+1, 15+13+10+3+2+1, 15+13+10+4+1, 15+13+10+5+1, 15+13+10+6+1, 15+13+10+7+1, 15+13+10+8+1, 15+13+11+1, 15+13+11+2+1, 15+13+11+3+1, 15+13+11+3+2+1, 15+13+11+4+1, 15+13+11+5+1, 15+13+11+6+1, 15+13+11+7+1, 15+13+11+8+1, 16+1, 16+2+1, 16+3+1, 16+3+2+1, 16+4+1, 16+5+1, 16+9+1, 16+9+2+1, 16+9+7+1, 16+11+1, 16+11+2+1, 16+11+3+1, 16+11+3+2+1, 16+11+4+1, 16+11+5+1, 16+11+6+1, 16+11+7+1, 16+11+8+1, 16+12+1, 16+12+2+1, 16+12+3+1, 16+12+3+2+1, 16+12+4+1, 16+12+5+1, 16+12+6+1, 16+12+7+1, 16+12+8+1, 16+12+9+1, 16+12+9+2+1, 16+12+9+7+1, 16+12+10+1, 16+12+10+2+1, 16+12+10+3+1, 16+12+10+3+2+1, 16+12+10+4+1, 16+12+10+5+1, 16+12+10+6+1, 16+12+10+7+1, 16+12+10+8+1, 16+12+11+1, 16+12+11+2+1, 16+12+11+3+1, 16+12+11+3+2+1, 16+12+11+4+1, 16+12+11+5+1, 16+12+11+6+1, 16+12+11+7+1, 16+12+11+8+1, 16+13+1, 16+13+2+1, 16+13+3+1, 16+13+3+2+1, 16+13+4+1, 16+13+5+1, 16+13+6+1, 16+13+7+1, 16+13+8+1, 16+13+9+1, 16+13+9+2+1, 16+13+9+7+1, 16+13+10+1, 16+13+10+2+1, 16+13+10+3+1, 16+13+10+3+2+1, 16+13+10+4+1, 16+13+10+5+1, 16+13+10+6+1, 16+13+10+7+1, 16+13+10+8+1, 16+13+11+1, 16+13+11+2+1, 16+13+11+3+1, 16+13+11+3+2+1, 16+13+11+4+1, 16+13+11+5+1, 16+13+11+6+1, 16+13+11+7+1, 16+13+11+8+1, 17+1, 17+2+1, 17+3+1, 17+3+2+1, 17+4+1, 17+5+1, 17+6+1, 17+9+1, 17+9+2+1, 17+9+7+1, 17+10+1, 17+10+2+1, 17+10+3+1, 17+10+3+2+1, 17+10+4+1, 17+10+5+1, 17+10+6+1, 17+10+7+1, 17+10+8+1, 17+11+1, 17+11+2+1, 17+11+3+1, 17+11+3+2+1, 17+11+4+1, 17+11+5+1, 17+11+6+1, 17+11+7+1, 17+11+8+1, 17+12+1, 17+12+2+1, 17+12+3+1, 17+12+3+2+1, 17+12+4+1, 17+12+5+1, 17+12+6+1, 17+12+7+1, 17+12+8+1, 17+12+9+1, 17+12+9+2+1, 17+12+9+7+1, 17+12+10+1, 17+12+10+2+1, 17+12+10+3+1, 17+12+10+3+2+1, 17+12+10+4+1, 17+12+10+5+1, 17+12+10+6+1, 17+12+10+7+1, 17+12+10+8+1, 17+12+11+1, 17+12+11+2+1, 17+12+11+3+1, 17+12+11+3+2+1, 17+12+11+4+1, 17+12+11+5+1, 17+12+11+6+1, 17+12+11+7+1, 17+12+11+8+1, 17+13+1, 17+13+2+1, 17+13+3+1, 17+13+3+2+1, 17+13+4+1, 17+13+5+1, 17+13+6+1, 17+13+7+1, 17+13+8+1, 17+13+9+1, 17+13+9+2+1, 17+13+9+7+1, 17+13+10+1, 17+13+10+2+1, 17+13+10+3+1, 17+13+10+3+2+1, 17+13+10+4+1, 17+13+10+5+1, 17+13+10+6+1, 17+13+10+7+1, 17+13+10+8+1, 17+13+11+1, 17+13+11+2+1, 17+13+11+3+1, 17+13+11+3+2+1, 17+13+11+4+1, 17+13+11+5+1, 17+13+11+6+1, 17+13+11+7+1, 17+13+11+8+1, 18+1, 18+4+1, 18+9+1, 18+9+2+1, 18+9+7+1, 18+10+1, 18+10+2+1, 18+10+3+1, 18+10+3+2+1, 18+10+4+1, 18+10+5+1, 18+10+6+1, 18+10+7+1, 18+10+8+1, 18+11+1, 18+11+2+1, 18+11+3+1, 18+11+3+2+1, 18+11+4+1, 18+11+5+1, 18+11+6+1, 18+11+7+1, 18+11+8+1, 18+12+1, 18+12+2+1, 18+12+3+1, 18+12+3+2+1, 18+12+4+1, 18+12+5+1, 18+12+6+1, 18+12+7+1, 18+12+8+1, 18+12+9+1, 18+12+9+2+1, 18+12+9+7+1, 18+12+10+1, 18+12+10+2+1, 18+12+10+3+1, 18+12+10+3+2+1, 18+12+10+4+1, 18+12+10+5+1, 18+12+10+6+1, 18+12+10+7+1, 18+12+10+8+1, 18+12+11+1, 18+12+11+2+1, 18+12+11+3+1, 18+12+11+3+2+1, 18+12+11+4+1, 18+12+11+5+1, 18+12+11+6+1, 18+12+11+7+1, 18+12+11+8+1, 18+13+1, 18+13+2+1, 18+13+3+1, 18+13+3+2+1, 18+13+4+1, 18+13+5+1, 18+13+6+1, 18+13+7+1, 18+13+8+1, 18+13+9+1, 18+13+9+2+1, 18+13+9+7+1, 18+13+10+1, 18+13+10+2+1, 18+13+10+3+1, 18+13+10+3+2+1, 18+13+10+4+1, 18+13+10+5+1, 18+13+10+6+1, 18+13+10+7+1, 18+13+10+8+1, 18+13+11+1, 18+13+11+2+1, 18+13+11+3+1, 18+13+11+3+2+1, 18+13+11+4+1, 18+13+11+5+1, 18+13+11+6+1, 18+13+11+7+1, 18+13+11+8+1, 18+16+1, 18+16+2+1, 18+16+3+1, 18+16+3+2+1, 18+16+4+1, 18+16+5+1, 18+16+9+1, 18+16+9+2+1, 18+16+9+7+1, 18+16+11+1, 18+16+11+2+1, 18+16+11+3+1, 18+16+11+3+2+1, 18+16+11+4+1, 18+16+11+5+1, 18+16+11+6+1, 18+16+11+7+1, 18+16+11+8+1, 18+16+12+1, 18+16+12+2+1, 18+16+12+3+1, 18+16+12+3+2+1, 18+16+12+4+1, 18+16+12+5+1, 18+16+12+6+1, 18+16+12+7+1, 18+16+12+8+1, 18+16+12+9+1, 18+16+12+9+2+1, 18+16+12+9+7+1, 18+16+12+10+1, 18+16+12+10+2+1, 18+16+12+10+3+1,

18+16+12+10+3+2+1, 18+16+12+10+4+1, 18+16+12+10+5+1, 18+16+12+10+6+1, 18+16+12+10+7+1, 18+16+12+10+8+1, 18+16+12+11+1, 18+16+12+11+2+1, 18+16+12+11+3+1, 18+16+12+11+3+2+1, 18+16+12+11+4+1, 18+16+12+11+5+1, 18+16+12+11+6+1, 18+16+12+11+7+1, 18+16+12+11+8+1, 18+16+13+1, 18+16+13+2+1, 18+16+13+3+1, 18+16+13+3+2+1, 18+16+13+4+1, 18+16+13+5+1, 18+16+13+6+1, 18+16+13+7+1, 18+16+13+8+1, 18+16+13+9+1, 18+16+13+9+2+1, 18+16+13+9+7+1, 18+16+13+10+1, 18+16+13+10+2+1, 18+16+13+10+3+1, 18+16+13+10+3+2+1, 18+16+13+10+4+1, 18+16+13+10+5+1, 18+16+13+10+6+1, 18+16+13+10+7+1, 18+16+13+10+8+1, 18+16+13+11+1, 18+16+13+11+2+1, 18+16+13+11+3+1, 18+16+13+11+3+2+1, 18+16+13+11+4+1, 18+16+13+11+5+1, 18+16+13+11+6+1, 18+16+13+11+7+1, 18+16+13+11+8+1, 18+17+1, 18+17+2+1, 18+17+3+1, 18+17+3+2+1, 18+17+4+1, 18+17+5+1, 18+17+6+1, 18+17+9+1, 18+17+9+2+1, 18+17+9+7+1, 18+17+10+1, 18+17+10+2+1, 18+17+10+3+1, 18+17+10+3+2+1, 18+17+10+4+1, 18+17+10+5+1, 18+17+10+6+1, 18+17+10+7+1, 18+17+10+8+1, 18+17+11+1, 18+17+11+2+1, 18+17+11+3+1, 18+17+11+3+2+1, 18+17+11+4+1, 18+17+11+5+1, 18+17+11+6+1, 18+17+11+7+1, 18+17+11+8+1, 18+17+12+1, 18+17+12+2+1, 18+17+12+3+1, 18+17+12+3+2+1, 18+17+12+4+1, 18+17+12+5+1, 18+17+12+6+1, 18+17+12+7+1, 18+17+12+8+1, 18+17+12+9+1, 18+17+12+9+2+1, 18+17+12+9+7+1, 18+17+12+10+1, 18+17+12+10+2+1, 18+17+12+10+3+1, 18+17+12+10+3+2+1, 18+17+12+10+4+1, 18+17+12+10+5+1, 18+17+12+10+6+1, 18+17+12+10+7+1, 18+17+12+10+8+1, 18+17+12+11+1, 18+17+12+11+2+1, 18+17+12+11+3+1, 18+17+12+11+3+2+1, 18+17+12+11+4+1, 18+17+12+11+5+1, 18+17+12+11+6+1, 18+17+12+11+7+1, 18+17+12+11+8+1, 18+17+13+1, 18+17+13+2+1, 18+17+13+3+1, 18+17+13+3+2+1, 18+17+13+4+1, 18+17+13+5+1, 18+17+13+6+1, 18+17+13+7+1, 18+17+13+8+1, 18+17+13+9+1, 18+17+13+9+2+1, 18+17+13+9+7+1, 18+17+13+10+1, 18+17+13+10+2+1, 18+17+13+10+3+1, 18+17+13+10+3+2+1, 18+17+13+10+4+1, 18+17+13+10+5+1, 18+17+13+10+6+1, 18+17+13+10+7+1, 18+17+13+10+8+1, 18+17+13+11+1, 18+17+13+11+2+1, 18+17+13+11+3+1, 18+17+13+11+3+2+1, 18+17+13+11+4+1, 18+17+13+11+5+1, 18+17+13+11+6+1, 18+17+13+11+7+1, 18+17+13+11+8+1, 19+1, 19+2+1, 19+3+1, 19+3+2+1, 19+4+1, 19+5+1, 19+6+1, 19+7+1, 19+8+1, 19+9+1, 19+9+2+1, 19+9+7+1, 19+12+1, 19+12+2+1, 19+12+3+1, 19+12+3+2+1, 19+12+4+1, 19+12+5+1, 19+12+6+1, 19+12+7+1, 19+12+8+1, 19+12+9+1, 19+12+9+2+1, 19+12+9+7+1, 19+12+10+1, 19+12+10+2+1, 19+12+10+3+1, 19+12+10+3+2+1, 19+12+10+4+1, 19+12+10+5+1, 19+12+10+6+1, 19+12+10+7+1, 19+12+10+8+1, 19+12+11+1, 19+12+11+2+1, 19+12+11+3+1, 19+12+11+3+2+1, 19+12+11+4+1, 19+12+11+5+1, 19+12+11+6+1, 19+12+11+7+1, 19+12+11+8+1, 19+13+1, 19+13+2+1, 19+13+3+1, 19+13+3+2+1, 19+13+4+1, 19+13+5+1, 19+13+6+1, 19+13+7+1, 19+13+8+1, 19+13+9+1, 19+13+9+2+1, 19+13+9+7+1, 19+13+10+1, 19+13+10+2+1, 19+13+10+3+1, 19+13+10+3+2+1, 19+13+10+4+1, 19+13+10+5+1, 19+13+10+6+1, 19+13+10+7+1, 19+13+10+8+1, 19+13+11+1, 19+13+11+2+1, 19+13+11+3+1, 19+13+11+3+2+1, 19+13+11+4+1, 19+13+11+5+1, 19+13+11+6+1, 19+13+11+7+1, 19+13+11+8+1, 20+1, 20+2+1, 20+3+1, 20+3+2+1, 20+4+1, 20+5+1, 20+6+1, 20+7+1, 20+8+1, 20+9+1, 20+9+2+1, 20+9+7+1, 20+12+1, 20+12+2+1, 20+12+3+1, 20+12+3+2+1, 20+12+4+1, 20+12+5+1, 20+12+6+1, 20+12+7+1, 20+12+8+1, 20+12+9+1, 20+12+9+2+1, 20+12+9+7+1, 20+12+10+1, 20+12+10+2+1, 20+12+10+3+1, 20+12+10+3+2+1, 20+12+10+4+1, 20+12+10+5+1, 20+12+10+6+1, 20+12+10+7+1, 20+12+10+8+1, 20+12+11+1, 20+12+11+2+1, 20+12+11+3+1, 20+12+11+3+2+1, 20+12+11+4+1, 20+12+11+5+1, 20+12+11+6+1, 20+12+11+7+1, 20+12+11+8+1, 20+13+1, 20+13+2+1, 20+13+3+1, 20+13+3+2+1, 20+13+4+1, 20+13+5+1, 20+13+6+1, 20+13+7+1, 20+13+8+1, 20+13+9+1, 20+13+9+2+1, 20+13+9+7+1, 20+13+10+1, 20+13+10+2+1, 20+13+10+3+1, 20+13+10+3+2+1, 20+13+10+4+1, 20+13+10+5+1, 20+13+10+6+1, 20+13+10+7+1, 20+13+10+8+1, 20+13+11+1, 20+13+11+2+1, 20+13+11+3+1, 20+13+11+3+2+1, 20+13+11+4+1, 20+13+11+5+1, 20+13+11+6+1, 20+13+11+7+1, 20+13+11+8+1, 21+1, 21+7+1, 21+19+1, 21+19+2+1, 21+19+3+1, 21+19+3+2+1, 21+19+4+1, 21+19+5+1, 21+19+6+1, 21+19+7+1, 21+19+8+1, 21+19+9+1, 21+19+9+2+1, 21+19+9+7+1, 21+19+12+1, 21+19+12+2+1, 21+19+12+3+1, 21+19+12+3+2+1, 21+19+12+4+1, 21+19+12+5+1, 21+19+12+6+1, 21+19+12+7+1, 21+19+12+8+1, 21+19+12+9+1, 21+19+12+9+2+1, 21+19+12+9+7+1, 21+19+12+10+1, 21+19+12+10+2+1, 21+19+12+10+3+1, 21+19+12+10+3+2+1, 21+19+12+10+4+1, 21+19+12+10+5+1, 21+19+12+10+6+1, 21+19+12+10+7+1, 21+19+12+10+8+1, 21+19+12+11+1, 21+19+12+11+2+1, 21+19+12+11+3+1, 21+19+12+11+3+2+1, 21+19+12+11+4+1, 21+19+12+11+5+1, 21+19+12+11+6+1, 21+19+12+11+7+1, 21+19+12+11+8+1, 21+19+13+1, 21+19+13+2+1, 21+19+13+3+1, 21+19+13+3+2+1, 21+19+13+4+1, 21+19+13+5+1, 21+19+13+6+1, 21+19+13+7+1, 21+19+13+8+1, 21+19+13+9+1, 21+19+13+9+2+1, 21+19+13+9+7+1, 21+19+13+10+1, 21+19+13+10+2+1, 21+19+13+10+3+1, 21+19+13+10+3+2+1, 21+19+13+10+4+1, 21+19+13+10+5+1, 21+19+13+10+6+1, 21+19+13+10+7+1, 21+19+13+10+8+1, 21+19+13+11+1, 21+19+13+11+2+1, 21+19+13+11+3+1, 21+19+13+11+3+2+1, 21+19+13+11+4+1, 21+19+13+11+5+1, 21+19+13+11+6+1, 21+19+13+11+7+1, 21+19+13+11+8+1, 21+20+1, 21+20+2+1, 21+20+3+1, 21+20+3+2+1, 21+20+4+1, 21+20+5+1, 21+20+6+1, 21+20+7+1, 21+20+8+1, 21+20+9+1, 21+20+9+2+1, 21+20+9+7+1, 21+20+12+1, 21+20+12+2+1, 21+20+12+3+1, 21+20+12+3+2+1, 21+20+12+4+1, 21+20+12+5+1, 21+20+12+6+1, 21+20+12+7+1, 21+20+12+8+1, 21+20+12+9+1, 21+20+12+9+2+1, 21+20+12+9+7+1, 21+20+12+10+1, 21+20+12+10+2+1, 21+20+12+10+3+1, 21+20+12+10+3+2+1, 21+20+12+10+4+1, 21+20+12+10+5+1, 21+20+12+10+6+1, 21+20+12+10+7+1, 21+20+12+10+8+1, 21+20+12+11+1, 21+20+12+11+2+1, 21+20+12+11+3+1, 21+20+12+11+3+2+1, 21+20+12+11+4+1, 21+20+12+11+5+1, 21+20+12+11+6+1, 21+20+12+11+7+1, 21+20+12+11+8+1, 21+20+13+1, 21+20+13+2+1, 21+20+13+3+1, 21+20+13+3+2+1, 21+20+13+4+1, 21+20+13+5+1, 21+20+13+6+1, 21+20+13+7+1, 21+20+13+8+1, 21+20+13+9+1, 21+20+13+9+2+1, 21+20+13+9+7+1, 21+20+13+10+1, 21+20+13+10+2+1, 21+20+13+10+3+1, 21+20+13+10+3+2+1, 21+20+13+10+4+1, 21+20+13+10+5+1, 21+20+13+10+6+1, 21+20+13+10+7+1, 21+20+13+10+8+1, 21+20+13+11+1, 21+20+13+11+2+1, 21+20+13+11+3+1, 21+20+13+11+3+2+1, 21+20+13+11+4+1, 21+20+13+11+5+1, 21+20+13+11+6+1, 21+20+13+11+7+1, 21+20+13+11+8+1, and 22+1; wherein the list above is not to be construed as limiting with respect to further embodiments which are also possible based on the dependencies of the embodiments 1) to 22) as disclosed hereinabove and which are also intended. In the list above the numbers refer to the embodiments according to their numbering provided hereinabove whereas "+" indicates the dependency from another embodiment. The different individualized embodiments are separated by commas. In other words, "3+2+1" for example refers to embodiment 3) depending on embodiment 2) depending on embodiment 1), i.e. embodiment "3+2+1" corresponds to embodiment 1) further limited by the features of embodiments 2) and 3).

The present invention also includes isotopically labelled, especially $^2$H (deuterium) labelled compounds of formula (I), which compounds are identical to the compounds of formula (I) except that one or more atoms have each been replaced by an atom having the same atomic number but an atomic mass different from the atomic mass usually found in nature. Isotopically labelled, especially $^2$H (deuterium) labelled compounds of formula (I) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula (I) are not isotopically labelled, or they are labelled only with one or more deuterium atoms. In a sub-embodiment, the compounds of formula (I) are not isotopically labelled at all. Isotopically labelled compounds of formula (I) may be prepared in analogy to the methods described hereinafter, but using the appropriate isotopic variation of suitable reagents or starting materials.

The term "pharmaceutically acceptable salts" refers to non-toxic, inorganic or organic acid and/or base addition salts, Lit. e.g. "Salt selection for basic drugs", *Int. J. Pharm.* (1986), 33, 201-217.

Where the plural form is used for compounds, salts, pharmaceutical compositions, diseases and the like, this is intended to mean also a single compound, salt, or the like.

The compounds of formula (I) according to any one of embodiments 1) to 22), or pharmaceutically acceptable salts thereof, are suitable for use as medicaments. In particular, compounds of formula (I) modulate the P2X$_7$ receptor, i.e. they act as P2X$_7$ receptor antagonists, and are useful for the prevention or treatment of diseases which are associated with the activation of the P2X$_7$ receptor such as pain; neurodegenerative and neuroinflammatory diseases; bone and joint diseases; obstructive diseases of the airways; cardiovascular diseases; eye diseases; skin diseases; abdominal and gastrointestinal tract diseases; genitourinary diseases; cancer; other auto-immune and allergic disorders; and other disorders with an inflammatory or immunological component.

In particular, the compounds of formula (I) according to any one of embodiments 1) to 22), or pharmaceutically acceptable salts thereof, are suitable for the prevention or treatment of pain. Pain refers to acute pain; chronic pain; pain associated with sprains and strains; chronic articular pain; pain associated with rheumatic fever; musculoskeletal pain; lower back and neck pain; inflammatory pain; neuropathic pain; visceral pain; pain associated with influenza or other viral infections; pain associated with cancer and tumor invasion; joint and bone pain; atypical facial pain; pain associated with migraine, toothache and dysmenorrhea; headache including tension headache and cluster headaches; pain associated with myocardial ischemia; pain associated with functional bowel disorders; sympathetically maintained pain; myositis; pain associated with cancer chemotherapy; and post operative pain.

Neuropathic pain includes especially diabetic neuropathy, sciatica, non-specific lower back pain, trigeminal neuralgia, multiple sclerosis pain, fibromyalgia, HIV-related neuropathy, post-herpetic neuralgia, and pain resulting from physical trauma, amputation, phantom limb syndrome, spinal surgery, cancer, toxins or chronic inflammatory conditions. In addition, neuropathic pain conditions include pain associated with normally non-painful sensations such as "pins and needles" (paraesthesias and dysesthesias), increased sensitivity to touch (hyperesthesia), painful sensation following innocuous stimulation (dynamic, static, thermal or cold allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

Chronic articular pain conditions include especially rheumatoid arthritis, osteoarthritis, rheumatoid spondylitis, gouty arthritis and juvenile arthritis.

Pain associated with functional bowel disorders includes especially non-ulcer dyspepsia, non-cardiac chest pain and irritable bowel syndrome.

Further, the compounds of formula (I) according to any one of embodiments 1) to 22), or pharmaceutically acceptable salts thereof, are suitable for the prevention or treatment of neurodegenerative and neuroinflammatory diseases. Neurodegenerative and neuro-inflammatory diseases include Alzheimer's disease and other dementing disorders including, but not limited to, Creutzfeldt-Jakob disease (CJD) and new variant Creutzfeldt-Jakob disease (nvCJD); Amyotrophic lateral sclerosis, amyloidosis; multiple sclerosis and other demyelinating syndromes; cerebral atherosclerosis and vasculitis; temporal arteritis; myasthenia gravis; Huntington's disease; Lewy Body dementia; and Parkinson's disease.

Further, the compounds of formula (I) according to any one of embodiments 1) to 22), or pharmaceutically acceptable salts thereof, are suitable for the prevention or treatment of bone and joint diseases. Bone and joint diseases include arthritides such as rheumatoid arthritis, osteoarthritis, gout or crystal arthropathy; intervertebral disc degeneration; temporomandibular joint degeneration; bone remodelling disease such as osteoporosis, Paget's disease or osteonecrosis; polychondritis; scleroderma; mixed connective tissue disorder; spondyloarthropathies; periodontal disease such as periodontitis; arthritides associated with or including osteoarthritis/osteoarthrosis, both primary and secondary to, for example, congenital hip dysplasia; cervical and lumbar spondylitis; Still's disease; seronegative spondyloarthropathies including ankylosing spondylitis, psoriatic arthritis, reactive arthritis and undifferentiated spondyloarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; Familial Mediterranean fever, Muckle-Wells syndrome, and Familial Hibernian Fever, Kikuchi disease; and drug-induced arthalgias, tendonitis, and myopathies including dystrophies and other inflammatory myopathies.

Further, the compounds of formula (I) according to any one of embodiments 1) to 22), or pharmaceutically acceptable salts thereof, are suitable for the prevention or treatment of obstructive diseases of the airways. Obstructive diseases of the airways include asthma, including bronchial, allergic, intrinsic, and extrinsic asthma, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; and acute viral infection including the common cold, and infection due to respiratory syncytial virus, influenza, coronavirus (including SARS) and adenovirus.

Further, the compounds of formula (I) according to any one of embodiments 1) to 22), or pharmaceutically acceptable salts thereof, are suitable for the prevention or treatment of cardiovascular diseases. Cardiovascular diseases include atherosclerosis, affecting the coronary and peripheral circulation; pericarditis; myocarditis; inflammatory and auto-immune cardiomyopathies including myocardial sarcoid; ischaemic reperfusion injuries; endocarditis, valvulitis, and aortitis including infective (for example syphilitic); vasculitides; and disorders of the proximal and peripheral veins including phlebitis and thrombosis, including deep vein thrombosis and complications of varicose veins.

Further, the compounds of formula (I) according to any one of embodiments 1) to 22), or pharmaceutically acceptable salts thereof, are suitable for the prevention or treatment of eye diseases. Eye diseases include blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; and infections of the eyes including viral, fungal, and bacterial infections.

Further, the compounds of formula (I) according to any one of embodiments 1) to 22), or pharmaceutically acceptable salts thereof, are suitable for the prevention or treatment of skin diseases. Skin diseases include psoriasis, skin burn, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia areata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; and drug-induced disorders including fixed drug eruptions.

Further, the compounds of formula (I) according to any one of embodiments 1) to 22), or pharmaceutically acceptable salts thereof, are suitable for the prevention or treatment of abdominal and gastrointestinal tract diseases. Abdominal and gastrointestinal tract diseases include hepatitis, including autoimmune, alcoholic and viral hepatitis; fibrosis and cirrhosis of the liver; cholecystitis; pancreatitis, both acute and chronic; non-inflammatory diarrhea; glossitis, gingivitis, periodontitis; oesophagitis, including reflux; eosinophilic gastro-enteritis, mastocytosis, Crohn's disease, colitis including ulcerative colitis, proctitis, pruritis ani; Coeliac disease, irritable bowel disease/syndrome, and food-related allergies which may have effects remote from the gut, for example migraine, rhinitis or eczema; allograft rejection including acute and chronic allograft rejection following, for example, transplantation of kidney, heart, liver, lung, bone marrow, skin or cornea or following blood transfusion; and chronic graft versus host disease;

Further, the compounds of formula (I) according to any one of embodiments 1) to 22), or pharmaceutically acceptable salts thereof, are suitable for the prevention or treatment of genitourinary diseases. Genitourinary diseases include nephritis including interstitial and glomerulonephritis; nephrotic syndrome; cystitis including acute and chronic (interstitial) cystitis and Hunner's ulcer; acute and chronic urethritis, hemorrhagic cystitis, prostatitis, epididymitis, oophoritis and salpingitis; vulvovaginitis; Peyronie's disease; and erectile dysfunction, both male and female.

Further, the compounds of formula (I) according to any one of embodiments 1) to 22), or pharmaceutically acceptable salts thereof, are suitable for the prevention or treatment of cancer. The treatment of cancer includes the treatment of brain tumors, prostate, lung, breast, ovarian, bowel and colon, stomach, pancreatic, skin and bone marrow (including leukaemias) and lymphoproliferative systems, such as non-Hodgkin's and Hodgkin's lymphoma; including the prevention and treatment of metastatic disease and tumor recurrences, and paraneoplastic syndromes.

Further, the compounds of formula (I) according to any one of embodiments 1) to 22), or pharmaceutically acceptable salts thereof, are suitable for the prevention or treatment of other auto-immune and allergic disorders. Other auto-immune and allergic disorders include Hashimoto's thyroiditis, Graves' disease, Addison's disease, diabetes mellitus, idiopathic thrombocytopaenic purpura, eosinophilic fasciitis, hyper-IgE syndrome, and antiphospholipid syndrome.

Further, the compounds of formula (I) according to any one of embodiments 1) to 22), or pharmaceutically acceptable salts thereof, are suitable for the prevention or treatment of other disorders with an inflammatory or immunological component. Other disorders with an inflammatory or immunological component include acquired immune deficiency syndrome (AIDS), leprosy, Sezary syndrome, and paraneoplastic syndromes.

Further, the compounds of formula (I) according to any one of embodiments 1) to 22), or pharmaceutically acceptable salts thereof, are suitable for the prevention or treatment of mood, depression, sleep and anxiety disorders.

Further, the compounds of formula (I) according to any one of embodiments 1) to 22), or pharmaceutically acceptable salts thereof, are suitable for the prevention or treatment of injury induced trauma and spinal cord injury.

Especially, compounds of formula (I) according to any one of embodiments 1) to 22), or pharmaceutically acceptable salts thereof, are suitable for the prevention or treatment of diseases selected from one, several or all of the following groups of diseases and disorders:

1) Pain, wherein pain refers to acute pain; chronic pain; pain associated with sprains and strains; chronic articular pain; pain associated with rheumatic fever; musculoskeletal pain; lower back and neck pain; inflammatory pain; neuropathic pain; visceral pain; pain associated with influenza or other viral infections; pain associated with cancer and tumor invasion; joint and bone pain; atypical facial pain; pain associated with migraine, toothache and dysmenorrhea; headache including tension headache and cluster headaches; pain associated with myocardial ischemia; pain associated with functional bowel disorders; sympathetically maintained pain; myositis; pain associated with cancer chemotherapy; and post operative pain;

Neuropathic pain includes especially diabetic neuropathy, sciatica, non-specific lower back pain, trigeminal neuralgia, multiple sclerosis pain, fibromyalgia, HIV-related neuropathy, post-herpetic neuralgia, trigeminal neuralgia, and pain resulting from physical trauma, amputation, phantom limb syndrome, spinal surgery, cancer, toxins or chronic inflammatory conditions. In addition, neuropathic pain conditions include pain associated with normally non-painful sensations such as "pins and needles" (paraesthesias and dysesthesias), increased sensitivity to touch (hyperesthesia), painful sensation following innocuous stimulation (dynamic, static, thermal or cold allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia);

Chronic articular pain conditions include especially rheumatoid arthritis, osteoarthritis, rheumatoid spondylitis, gouty arthritis and juvenile arthritis; Pain associated with functional bowel disorders includes especially non-ulcer dyspepsia, non-cardiac chest pain and irritable bowel syndrome;

2) Neurodegenerative and neuro-inflammatory diseases such as Alzheimer's disease and other dementing disorders including, but not limited to, Creutzfeldt-Jakob disease (CJD) and new variant Creutzfeldt-Jakob disease (nvCJD); amyloidosis; Amyotrophic lateral sclerosis, multiple sclerosis and other demyelinating syndromes; cerebral atherosclerosis and vasculitis; temporal arteritis; myasthenia gravis; Huntington's disease; Lewy Body dementia; and Parkinson's disease;

3) Bone and joint diseases such as arthritides such as rheumatoid arthritis, osteoarthritis, gout or crystal arthropathy; intervertebral disc degeneration; temporomandibular joint degeneration; bone remodelling disease such as osteoporosis, Paget's disease or osteonecrosis; polychondritis; scleroderma; mixed connective tissue disorder; spondyloarthropathies; periodontal disease such as periodontitis; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositis and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; Muckle-Wells syndrome, and Familial Hibernian Fever, Kikuchi disease; and drug-induced arthalgias, tendonitis, and myopathies;

4) Obstructive diseases of the airways such as chronic obstructive pulmonary disease (COPD); cystic fibrosis; lung emphysema; sarcoidosis; farmer's lung and related diseases; lung fibrosis, including fibrosis complicating tuberculosis; and chronic cough associated with inflammatory and secretory conditions of the airways;

5) Cardiovascular diseases such as inflammatory and auto-immune cardiomyopathies;

6) Eye diseases such as degenerative or inflammatory disorders affecting the retina;

7) Skin diseases such as psoriasis, skin burn, atopic dermatitis, contact dermatitis or other eczematous dermatoses; and discoid lupus erythematosus;

8) Abdominal and gastrointestinal tract diseases such as fibrosis and cirrhosis of the liver; cholecystitis; pancreatitis, both acute and chronic; Crohn's disease; colitis including ulcerative colitis; and irritable bowel disease/syndrome;

9) Genitourinary diseases such as nephritis including interstitial and glomerulonephritis; nephrotic syndrome; and cystitis including acute and chronic (interstitial) cystitis; and 10) Other auto-immune and allergic disorders such as Hashimoto's thyroiditis, Graves' disease, Addison's disease, diabetes mellitus, idiopathic thrombocytopaenic purpura, eosinophilic fasciitis, hyper-IgE syndrome, and antiphospholipid syndrome.

Most preferably, compounds of formula (I) according to any one of embodiments 1) to 22), or pharmaceutically acceptable salts thereof, are suitable for the prevention or treatment of diseases selected from one, several or all of the following groups of diseases and disorders:

1) Pain, wherein pain refers to acute pain; chronic pain; pain associated with sprains and strains; chronic articular pain; pain associated with rheumatic fever; musculoskeletal pain (preferred); lower back and neck pain; inflammatory pain; neuropathic pain (preferred); visceral pain; pain associated with influenza or other viral infections; pain associated with cancer and tumor invasion; joint and bone pain; atypical facial pain; pain associated with migraine, toothache and dysmenorrhea; headache including tension headache and cluster headaches; pain associated with myocardial ischemia; pain associated with functional bowel disorders; sympathetically maintained pain; myositis; pain associated with cancer chemotherapy; and post operative pain;

Neuropathic pain includes especially diabetic neuropathy, sciatica, non-specific lower back pain, trigeminal neuralgia, multiple sclerosis pain, fibromyalgia, HIV-related neuropathy, post-herpetic neuralgia, trigeminal neuralgia, and pain resulting from physical trauma, amputation, phantom limb syndrome, spinal surgery, cancer, toxins or chronic inflammatory conditions. In addition, neuropathic pain conditions include pain associated with normally non-painful sensations such as "pins and needles" (paraesthesias and dysesthesias), increased sensitivity to touch (hyperesthesia), painful sensation following innocuous stimulation (dynamic, static, thermal or cold allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia);

Chronic articular pain conditions include especially rheumatoid arthritis, osteoarthritis, rheumatoid spondylitis, gouty arthritis and juvenile arthritis; Pain associated with functional bowel disorders includes especially non-ulcer dyspepsia, non-cardiac chest pain and irritable bowel syndrome;

2) Rheumatoid arthritis and osteoarthritis;
3) Chronic obstructive pulmonary disease (COPD); and
4) Crohn's disease.

The invention also relates to the use of a compound of formula (I) according to any one of embodiments 1) to 22) for the preparation of pharmaceutical compositions for the treatment and/or prophylaxis of the above-mentioned diseases.

The present invention also relates to pharmaceutically acceptable salts and to pharmaceutical compositions and formulations of compounds of formula (I) according to any one of embodiments 1) to 22).

A pharmaceutical composition according to the present invention contains at least one compound of formula (I) according to any one of embodiments 1) to 22) (or a pharmaceutically acceptable salt thereof) as the active agent and optionally carriers and/or diluents and/or adjuvants.

The compounds of formula (I) according to any one of embodiments 1) to 22) and their pharmaceutically acceptable salts can be used as medicaments, e.g. in the form of pharmaceutical compositions for enteral (such as especially oral) or parenteral administration (including topical application or inhalation).

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formula (I) according to any one of embodiments 1) to 22), or a pharmaceutically acceptable salt thereof.

Any reference to a compound of formula (I), $(I_{St1})$, $(I_{St2})$ and $(I_{St3})$, in this text is to be understood as referring also to the salts (and especially the pharmaceutically acceptable salts) of such compounds, as appropriate and expedient. The preferences indicated for the compounds of formula (I) of course apply mutatis mutandis to the compounds of formula $(I_{St1})$, of formula $(I_{St2})$ and of formula $(I_{St3})$ as well as to the salts and pharmaceutically acceptable salts of the compounds of formula (I), of formula $(I_{St1})$, of formula $(I_{St2})$ and of formula $(I_{St3})$. The same applies to these compounds as medicaments, to pharmaceutical compositions containing these compounds as active principles or to the uses of these compounds for the manufacture of a medicament for the treatment of the diseases according to this invention.

Unless used regarding temperatures, the term "about" (or alternatively "around") placed before a numerical value "X" refers in the current application to an interval extending from X minus 10% of X to X plus 10% of X, and preferably to an interval extending from X minus 5% of X to X plus 5% of X. In the particular case of temperatures, the term "about" (or alternatively "around") placed before a temperature "Y" refers in the current application to an interval extending from the temperature Y minus 10° C. to Y plus 10° C., and preferably to an interval extending from Y minus 5° C. to Y plus 5° C. Besides, the term "room temperature" (RT) as used herein refers to a temperature of about 25° C.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

The compounds of Formula (I) can be manufactured by the methods given below, by the methods given in the Examples or by analogous methods. Optimum reaction conditions may vary with the particular reactants or solvents used, but such conditions can be determined by a person skilled in the art by routine optimisation procedures.

If not indicated otherwise, the generic groups $R^1$, $R^2$, $R^3$, $R^4$, n and X are as defined for formula (I). Other abbreviations used are defined in the experimental section.

In some instances the generic groups $R^1$, $R^2$, $R^3$, $R^4$, n and X might be incompatible with the assembly illustrated in the schemes below and will therefore require the use of protecting groups (PG). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups are as necessary in place.

Preparation of Compounds of Formula (I):

Compounds of formula (I) can be prepared by reaction of a carboxylic acid (II) with an amine (III) using standard amide coupling reagents such as EDC.HCl/HOBt, SiliaBond® carbodiimide/HOAt, HATU/HOAt or PyBOP and a base like DIPEA in a solvent like DCM, THF or DMF preferably at temperatures between RT and 45° C. (scheme 1).

Scheme 1: Synthesis of compounds of formula (I)

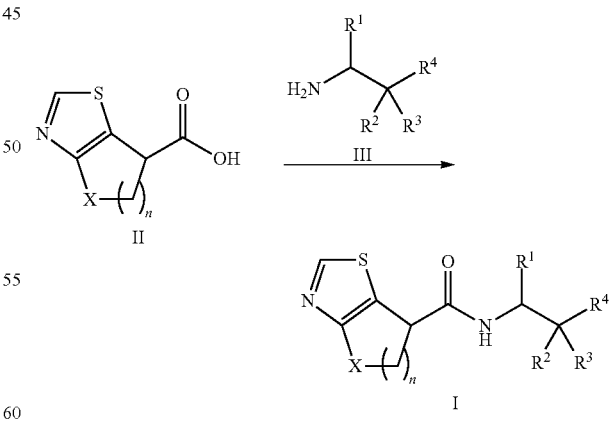

Compounds of formula (II), if not commercially available, can be prepared following the procedures outlined in the schemes below and in the experimental part.

Compounds of formula (II), wherein X represents —$CH_2$— can be prepared from a methyl ester (IV) like, for instance, methyl cyclohex-2-enecarboxylate (Bioorg. Med.

Chem. 1999, 7, 1505-1511) by a bromohydrin-formation/ oxidation sequence using (1) NBS in a THF/H$_2$O mixture at temperatures around RT and (2) an oxidant such as DMP in a solvent like DCM at temperatures around RT to form α-bromoketone (V) (scheme 2). Condensation with thioformamide in a solvent such as dioxane at temperatures between 60° C. and 110° C. provide thiazoles (VII). Thioformamide (VI) can be prepared from formamide with P$_4$S$_{10}$ in a solvent such as dioxane at temperatures between 60° C. and 110° C. Saponification of the methyl ester (VII) can be performed under standard conditions such as LiOH in a THF/MeOH/H$_2$O mixture, preferably at temperatures between 0° C. and 45° C. to form compounds of formula (IIa).

Scheme 2: Synthesis of compounds of formula (IIa)

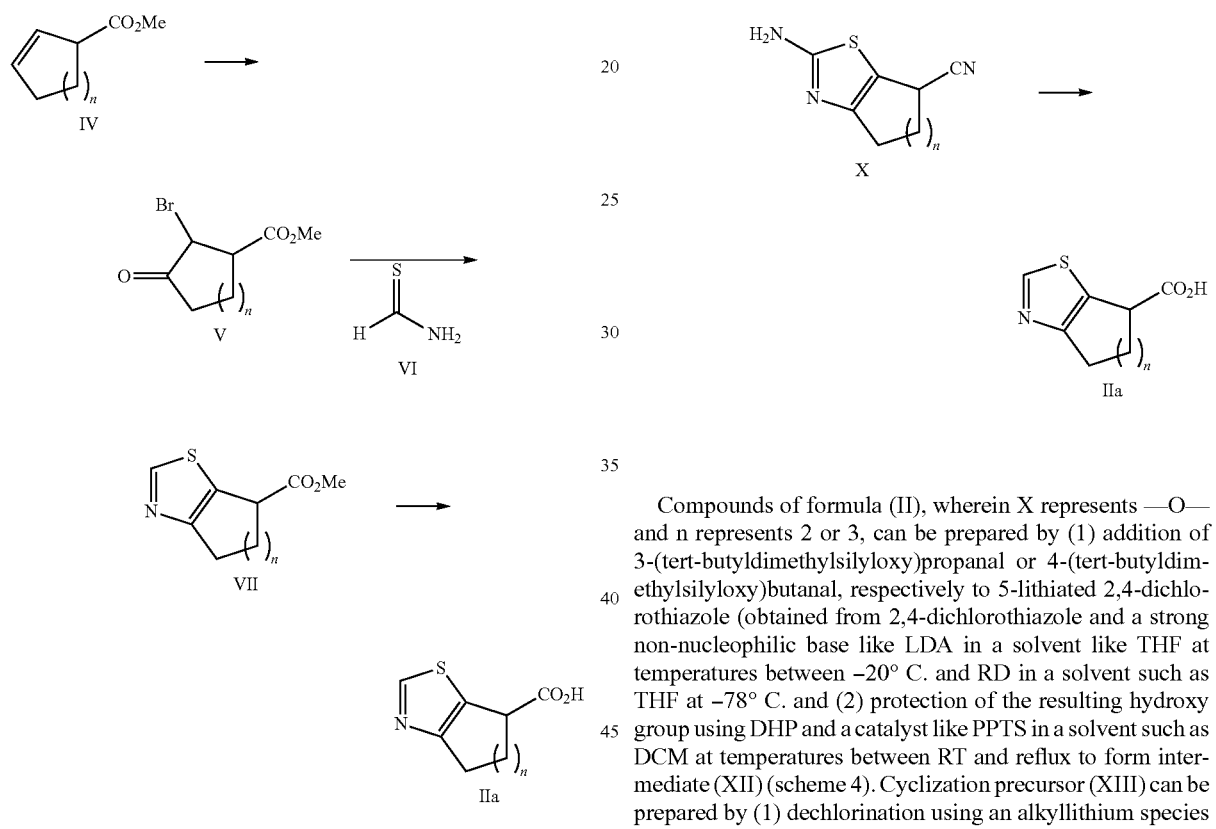

Scheme 3: Synthesis of compounds of formula (IIa)

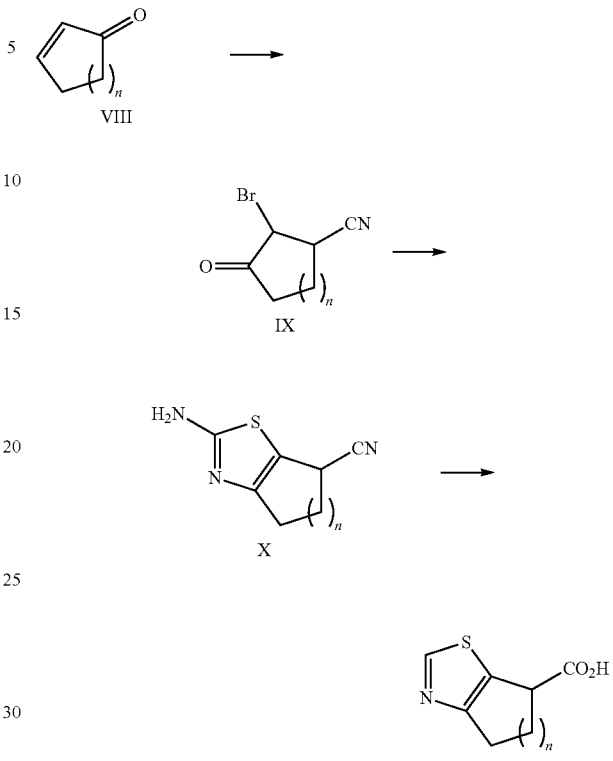

Alternatively, compounds of formula (II), wherein X represents —CH$_2$— can be prepared from the corresponding cycloalk-2-enone (VIII) by (1) addition of TMS-CN, catalyzed by Ni(cod)$_2$ and Gd(OTf)$_3$ in the presence of norbornadiene in a solvent such as THF at temperatures around RT and (2) bromination of the resulting silylenolether using an electrophilic bromine source such as NBS in a THF/H$_2$O mixture at temperatures around 0° C. to form α-bromoketone (IX) (scheme 3). The aminothiazoles (X) are prepared by condensation of the corresponding α-bromoketone (IX) with thiourea in a solvent such as dioxane at temperatures between 60° C. and 100° C. The aminothiazoles of formula (X) can be diazotized utilizing tBu-nitrite in THF at temperatures between 60° C. and 80° C. to provide the corresponding thiazoles. Hydrolysis of the nitrile group using aq. conc. HCl at temperatures between 60° C. and 100° C. form carboxylic acids (IIa).

Compounds of formula (II), wherein X represents —O— and n represents 2 or 3, can be prepared by (1) addition of 3-(tert-butyldimethylsilyloxy)propanal or 4-(tert-butyldimethylsilyloxy)butanal, respectively to 5-lithiated 2,4-dichlorothiazole (obtained from 2,4-dichlorothiazole and a strong non-nucleophilic base like LDA in a solvent like THF at temperatures between −20° C. and RD in a solvent such as THF at −78° C. and (2) protection of the resulting hydroxy group using DHP and a catalyst like PPTS in a solvent such as DCM at temperatures between RT and reflux to form intermediate (XII) (scheme 4). Cyclization precursor (XIII) can be prepared by (1) dechlorination using an alkyllithium species such as nBuLi in a solvent like THF at temperatures between −100° C. and −40° C. and (2) treatment with a fluoride source such as TBAF in a solvent like THF at temperatures between 0° C. and RT. Cyclization to compounds of formula (XIV) can be performed with a base such as NaH or KOtBu in a solvent like DMF or tBuOH, respectively, or through a palladium mediated procedure using Pd(OAc)$_2$, rac-2-(di-tert-butylphosphino)-1,1'-binaphthyl and a base like Cs$_2$CO$_3$ in a solvent such as toluene at temperatures between 80° C. and 110° C. Compounds of formula (IIb) are obtained by (1) removal of the THP protecting group under acidic conditions using, for instance, catalytic amounts of PTSA in a solvent mixture like THF/H$_2$O at temperatures around RT, (2) a Mitsunobu reaction, and (3) hydrolysis of the nitrile using aq. conc. HCl at temperatures between 60° C. and 100° C. The Mitsunobu reaction can be carried out with acetone cyanohydrin, (nBu)$_3$P and 1,1'-(azodicarbonyl)dipiperidine in a solvent like THF at temperatures between 0° C. and RT.

Scheme 4: Synthesis of compounds of formula (IIb) wherein n represents 2 or 3

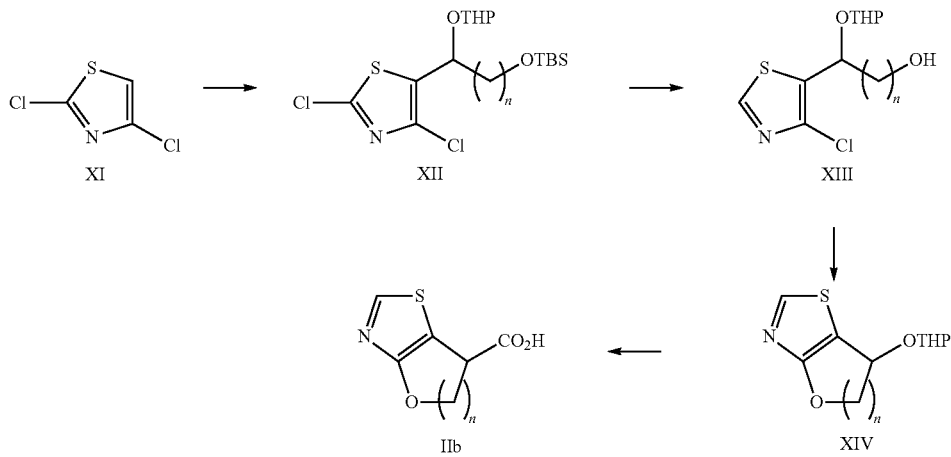

Compound of formula (II), wherein X represents —O— and n represents 1 can be prepared by reaction of 4-bromothiazole (XV) with the sodium salt of DL-1,2-isopropylideneglycerol at temperatures between 120° C. and 150° C. and subsequent bromination with an electrophilic bromine source such as NBS in a solvent like MeCN at temperatures between 0° C. and RT (scheme 5). The resulting 5-bromothiazole (XVI) is sequentially treated with (1) catalytic amounts of an acid such as PPTS in a solvent like MeOH at temperatures around reflux, (2) trimethyl orthoformate in a solvent like DCM at temperatures around RT, (3) AcBr in a solvent like DCM at temperatures around RT, and (4) a carbonate base such as $K_2CO_3$ in a solvent like MeOH at temperatures around RT to form oxirane (XVII). At temperatures between −78° C. and RT, a soln. of oxirane (XVII) in an ether solvent like THF is consecutively treated with an alkyl lithium reagent like nBuLi, a trialkylsilyl chloride like TIPSCl, and again with an alkyl lithium reagent like nBuLi to form dihydrofurothiazole (XVIII). A two-step oxidation procedure utilizing (1) DMP in a solvent like DCM at temperatures between 0° C. and RT and (2) sodium chlorite in a buffered aq. solution with tBuOH as co-solvent and 2-methyl-2-butene as scavenger at temperatures around 0° C. provides carboxylic acid (XIX). Removal of the silyl protecting group to form a compound of formula (IIc) can be performed with a fluoride source such as TBAF in a solvent like THF at temperatures between 0° C. and RT.

Scheme 5: Synthesis of compound of formula (IIc)

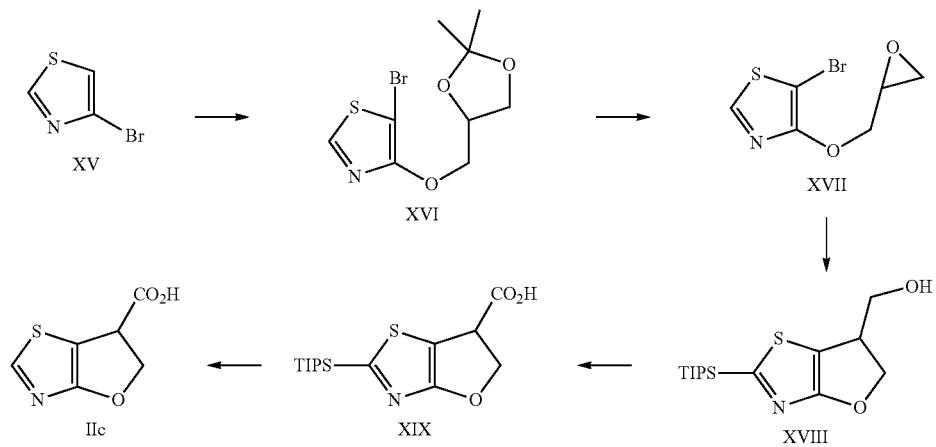

If not commercially available, amines of formula III can be prepared according to procedures described in WO2009/132000, outlined in the schemes below and in the experimental part.

Amino nitriles of formula (XX), wherein $NR^5R^6$ represents heterocyclyl which is unsubstituted or mono- or disubstituted with fluoro and $R^4$ represents heteroaryl (scheme 6) can be prepared by Strecker reaction between aldehydes of formula (XXI) and amines of formula $R^5R^6NH$ in the presence of a suitable cyanating reagent such as TMS-CN and a suitable Lewis acid catalyst such as $ZnI_2$ in a suitable mixture of solvents such as $Et_2O$/MeOH at temperatures between 0° C. and 80° C. The resulting nitriles of formula (XX) can be transformed to diamines of formula (IIIa) (scheme 6) by reduction under hydrogenation conditions in the presence of a suitable catalyst such as Raney nickel and a suitable solvent such as methanolic ammonia at temperatures around RT.

Scheme 6: Synthesis of amines of formula (IIIa), wherein $R^4$ represents heteroaryl and wherein $NR^5R^6$ represents heterocyclyl

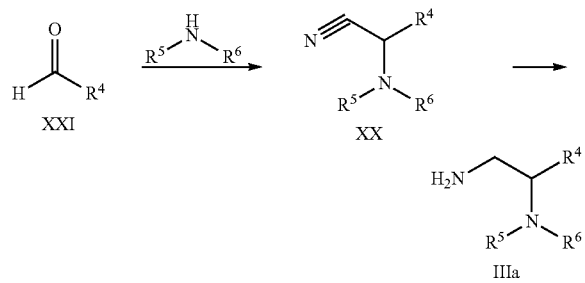

Scheme 7: Synthesis of amines of formula (IIIb), wherein $R^4$ represents heteroaryl and wherein $R^5$ and $R^6$, together with the carbon atom to which they are attached, represent heterocycl

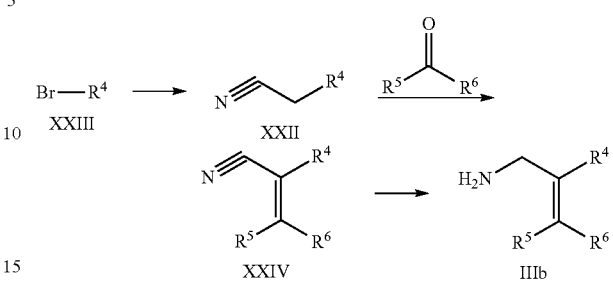

If not commercially available, nitriles of formula (XXII), wherein $R^4$ represents heteroaryl (scheme 7) can be prepared by a two step procedure: (i) heteroarylation of methylcyanoacetate by treatment with a bromoheteroarene of formula Br—$R^4$ in the presence of a suitable base such as KOtBu, a suitable palladium catalyst such as Pd(OAc)$_2$, a suitable ligand such as dppf in a suitable solvent such as dioxane as described in J. Org. Chem. 2008, 73, 1643-1645 and (ii) subsequent decarboxylation of the isolated methyl heteroarylcyanoacetate intermediates by treatment with a suitable salt such as LiCl in a suitable mixture of solvents such as DMSO/water at temperatures around 140° C.

Alternatively, if not commercially available, nitriles of formula (XXII), wherein $R^4$ represents heteroaryl can be prepared according to J. Am. Chem. Soc. 2011, 133, 6948-6951.

Cyano alkenes of formula (XXIV) (scheme 7) wherein $R^5$ and $R^6$ form, together with the carbon atom to which they are attached, a heterocyclyl group which is unsubstituted or mono- or di-substituted with fluoro can be prepared by Knoevenagel condensation of heteroaryl-acetonitriles of formula (XXII) with ketones of formula $R^5COR^6$ by treatment with a suitable base such as KOH or NaOMe in a suitable solvent such as MeOH at temperatures between 0° C. and 60° C.

The respective amines of formula (IIIb) (scheme 7) can be prepared by reduction of cyano alkenes of formula (XXIV) using a two step procedure: (i) hydrogenation in the presence of a suitable catalyst such as Pd/C followed by (ii) hydrogenation in the presence of a suitable catalyst such as Raney nickel, both steps being carried out in a suitable solvent such as methanolic ammonia at temperatures around RT.

Alternatively, amines of formula (IIIb) can be prepared by reduction of cyano alkenes of formula (XXIV) in the presence of a suitable reducing reagent such as BH$_3$ THF complex in a suitable solvent such as THF at temperatures around 60° C.

If not commercially available, heteroaryl-acetonitriles of formula (XXII), wherein $R^4$ represents heteroaryl (scheme 8) can be prepared from bromoheteroarene of formula Br—$R^4$ by a two step procedure as described above.

Nitriles of formula (XXV) (scheme 8) can be prepared by dialkylation of heteroaryl-acetonitriles of formula (XXII) with dihaloalkanes such as Br—(CH$_2$)$_m$—CR$^7$R$^8$—(CH$_2$)$_2$—Br, wherein m represents 1, 2 or 3 and $R^7$ and $R^8$ represent hydrogen or fluoro, in the presence of a base such as NaH or tBuOK in a suitable organic solvent such as THF or DMSO preferably at temperatures between 0° C. and RT.

Amines of formula (IIIc) (scheme 8) can be prepared by reduction of nitriles of formula (XXV) for instance under hydrogenation conditions in the presence of a suitable catalyst such as Raney nickel and a suitable solvent such as methanolic ammonia at temperatures around RT or with a suitable reducing reagent such as BH$_3$ THF complex in a suitable solvent such as THF at temperatures around 70° C.

Amines of formula (IIIc), wherein m represents 2 and $R^7$ and $R^8$ represent fluoro (scheme 8) can be prepared for instance following a 4-step sequence: (i) tandem double Michael addition-Dieckmann condensation reaction of acetonitrile derivatives of formula (XXII) with methyl acrylate according to J. Org. Chem., 2007, 72, 7455-7458 (ii) Krapcho decarboxylation of intermediates of formula (XXVI) following conditions as those already described above for the synthesis of compounds of formula (XXII) (iii) difluorination of ketone intermediates of formula (XXVII) using DAST in a suitable solvent such as DCM at temperatures between −78° C. and RT and (iv) reduction of nitriles of formula (XXVIII) following conditions such as those already described for the synthesis of amines of formula (IIIc) from (XXV).

Scheme 8: Synthesis of amines of formula (IIIc), wherein $R^4$ represents heteroaryl, wherein $R^7$ and $R^8$ represent hydrogen or fluoro and wherein m represents 1,2 or 3

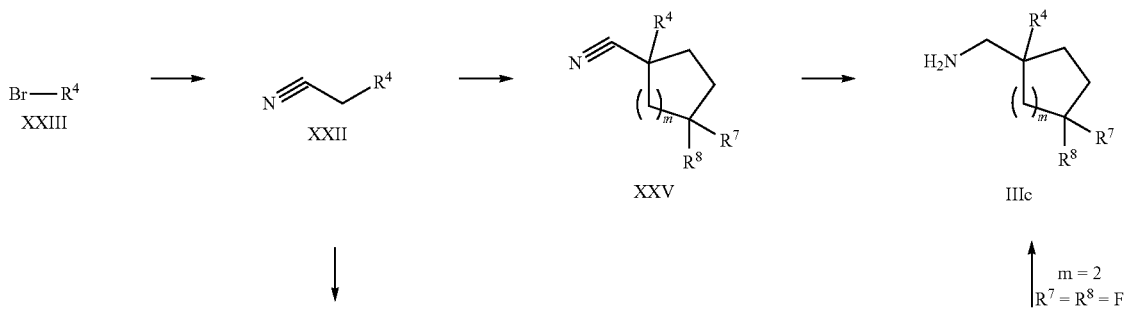

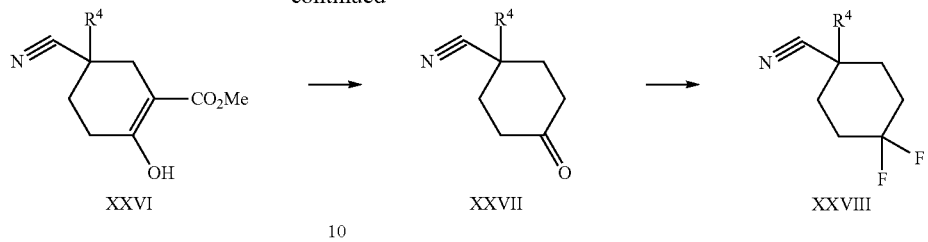

If not commercially available, amines of formula (XXX), wherein $R^9$ and $R^{19}$ represent hydrogen and m represents 1, 2 or 3 (scheme 9) can be prepared for instance by alkylation of N-(diphenylmethylene)glycine tert-butyl ester with cycloalkyl bromide or iodide of formula (XXIX) (X represents bromo or iodo) according to Angew. Chem. Int. Ed., 2005, 44, 1549-1551. Subsequent reduction of resulting esters of formula (XXX) using for instance lithium aluminum hydride in a suitable solvent such as THF at temperatures between 0° C. and RT gives aminoalcohols of formula (IIId) wherein $R^7$ and $R^8$ represent hydrogen.

If not commercially available, amines of formula (XXX), wherein $R^9$ represents hydroxy, $R^{10}$ represents hydrogen and m represents 1, 2 or 3 or $R^9$ and $R^{10}$ form an ethylenedioxy group and m represents 1, 2 or 3 (scheme 9) can be prepared as previously described for the synthesis of amines of formula (XXX) wherein $R^9$ and $R^{10}$ represent hydrogen.

If not commercially available as methyl ester ($R^{11}$ represents Me), compounds of formula (XXXI), wherein $R^{11}$ represents tBu and $R^{12}$ represents Boc (or Z respectively) (scheme 9) can be prepared by treatment of amines of formula (XXX) wherein $R^9$ represents hydroxy and $R^{10}$ represents hydrogen with Boc-anhydride (or Z—Cl respectively) in the presence of a base such as $Et_3N$ or NaOH in a suitable solvent such as DCM or dioxane/water at temperatures between 0° C. and RT. Oxidation of resulting compounds using for instance DMP in a suitable solvent such as DCM at temperatures around RT gives ketones of formula (XXXII), wherein $R^{11}$ represents tBu or Me and $R^{12}$ represents Boc or Z.

Alternatively, ketones of formula (XXXII), wherein $R^{11}$ represents tBu or Me and $R^{12}$ represents Z (scheme 9) can be prepared by a two step procedure: (i) Z-protection of amines of formula (XXX), wherein $R^9$ and $R^{10}$ form an ethylenedioxy group using conditions as previously described for the synthesis of compounds of formula (XXXI) and (ii) cleavage of the ketal protecting group using acidic conditions such as aq. HCl and a suitable organic solvent such as MeCN or THF at temperatures around RT.

If not commercially available, compounds of formula (XXXIII), wherein $R^{11}$ represents tBu or Me and $R^{12}$ represents Boc or Z (scheme 9) can be prepared by fluorination of ketones of formula (XXXII) wherein $R^{11}$ represents tBu or Me and $R^{12}$ represents Boc or Z using a fluorinating reagent such as DAST or bis(2-methoxyethyl)aminosulfur trifluoride in the presence of a suitable solvent such as THF or DCM at temperatures between 0° C. and RT.

Compounds of formula (XXXIV), wherein $R^{12}$ represents Boc or Z (scheme 9) can be prepared by reduction of esters of formula (XXXIII) wherein $R^{11}$ represents tBu or Me and $R^{12}$ represents Boc or Z following conditions such as those already described for the reduction of esters of formula (XXX) wherein $R^9$ and $R^{10}$ represent hydrogen.

Amines of formula (IIId), wherein $R^7$ and $R^8$ represent fluoro and m represents 1, 2 or 3 (scheme 9) can be prepared by Boc cleavage (or Z cleavage respectively) from compounds of formula (XXXIV) wherein $R^{12}$ represents Boc (or Z respectively) using a suitable acid such as HCl or TFA in the presence of a suitable solvent such as dioxane, EtOAc or DCM (or under hydrogenation conditions in the presence of a suitable catalyst such as palladium on charcoal and a suitable solvent such as MeOH or dioxane respectively) at temperatures around RT.

Amines of formula (IIId), wherein $R^7$ represents fluoro, $R^8$ represents hydrogen and m represents 1, 2 or 3 can be prepared by fluorination of compounds of formula (XXXI), wherein $R^{11}$ represents tBu or Me and $R^{12}$ represents Boc or Z with for instance DAST in a solvent like DCM at temperatures between −78° C. and RT, followed by (1) reduction of the ester following conditions such as those already described for the reduction of esters of formula (XXX), wherein $R^9$ and $R^{19}$ represent hydrogen and (2) removal of Boc (or Z, respectively) following conditions such as those already described for compounds of formula (XXXIV).

Scheme 9: Synthesis of amines of formula (IIId), wherein $R^7$ and $R^8$ represent hydrogen or fluoro and wherein m represents 1, 2 or 3.

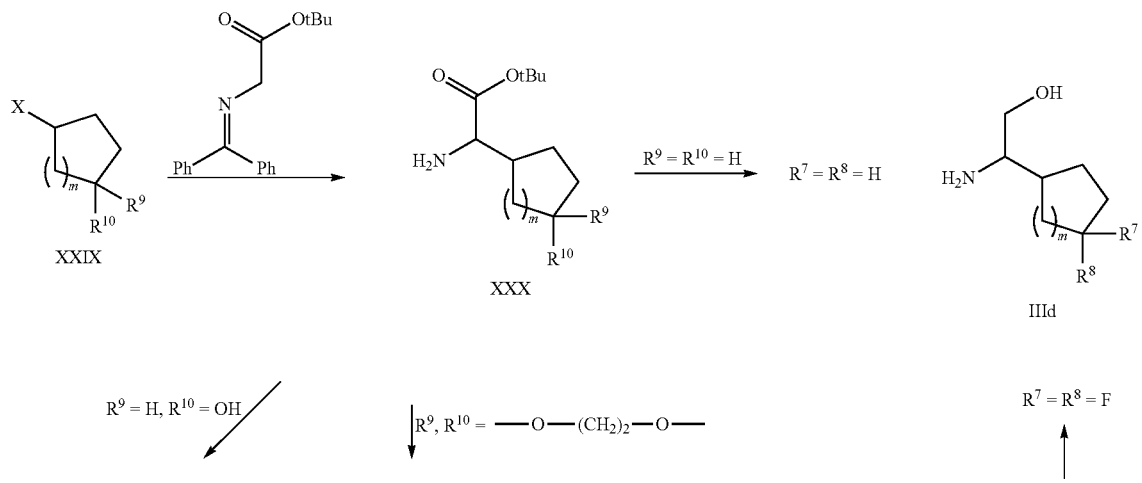

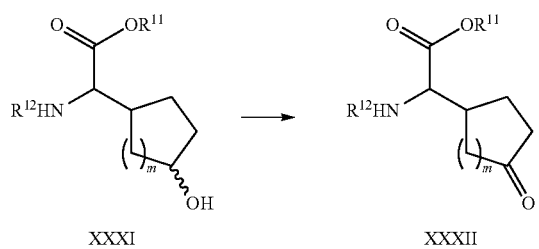
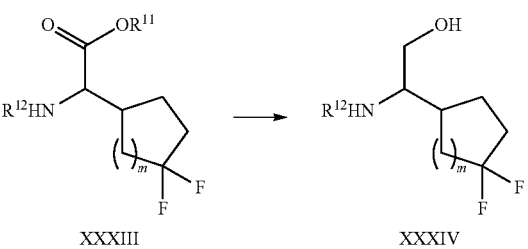

EXPERIMENTAL PART

Abbreviations (as Used Herein and in the Description Above)
Ac acetyl
anh. anhydrous
aq. aqueous
Boc tert-butoxycarbonyl
nBu n-butyl
tBu tert-butyl
CC column chromatography
cod 1,5-cyclooctadiene
conc. concentrated
comb. combined
DAST diethylaminosulfur trifluoride
dba dibenzylideneacetone
DCM dichloromethane
DHP 3,4-dihydro-2H-pyran
DIPA diisopropylamine
DIPEA diisopropylethylamine
DMF dimethylformamide
DMP Dess-Martin periodinane
DMSO dimethyl sulfoxide
dppf 1,1'-bis(diphenylphosphino)ferrocene
Et ethyl
EDC.HCl N-(3-dimethylaminopropyl)-N'-ethylcarbodiimide hydrochloride
h hour(s)
HATU O-(7-azabenzotriazol-1-yl)-N,N,N',N'-tetramethyluronium hexafluorophosphate
Hept heptane
HOAt 1-hydroxy-7-azabenzotriazole
HOBt 1-hydroxybenzotriazole hydrate
HV high vacuum
LC-MS liquid chromatography-mass spectrometry
LDA lithium diisopropylamide
M molar
Me methyl
MeCN acetonitrile
min minute(s)
NBS N-bromosuccinimide
NMR nuclear magnetic resonance
org. organic
PPTS pyridinium p-toluenesulfonate
PTSA p-toluenesulfonic acid
PyBOP (benzotriazol-1-yloxy)tripyrrolidinophosphonium hexafluorophosphate
RT room temperature
sat. saturated
soln. solution
TBAF tetra-n-butylammonium fluoride
TBS tert-butyldimethylsilyl
Tf trifluoromethanesulfonyl
TFA trifluoroacetic acid
THF tetrahydrofuran
THP tetrahydropyran
TIPS triisopropylsilyl
TMS trimethylsilyl
$t_R$ retention time
UV ultra-violet
Vis visible
Z benzyloxycarbonyl A. Characterization Methods Used
Nuclear Magnetic Resonance:
Brucker Avance 400, 400 MHz; chemical shifts are given in ppm relative to the solvent used; multiplicities: s=singlet, d=doublet, t=triplet, q=quadruplet, m=multiplet, br=broad, coupling constants are given in Hz.
Analytical HPLC-MS Methods:
HPLC-MS analyses were performed on a Thermo MSQ mass spectrometer with a Dionex Ultimate HPG-3000 pump and a Dionex Ultimate 3000 photodiode array detector.
(1) eluents: A: $H_2O$+0.05% HCOOH, B: $CH_3CN$; gradient: 5% B→95% B (0.0 min-2.0 min), 95% B (2.0 min-2.3 min); flow: 1.8 mL/min; detection: UV/Vis+MS, $t_R$ is given in min; column: Ascentis Express C18, 2.7 um, 2.1×50 mm.
(2) eluents: A: $H_2O$+0.05% $NH_4OH$, B: $CH_3CN$; gradient: 5% B→95% B (0.0 min 2.0 min), 95% B (2.0 min-2.3 min); flow: 1.8 mL/min; detection: UV/Vis+MS, $t_R$ is given in min; column: Ascentis Express O18, 2.7 um, 2.1×50 mm.
HPLC-MS analyses were performed on a Thermo MSQ Plus mass spectrometer with a Dionex HPG-3200RS pump (or Agilent G4220A) and a Dionex DAD-3000RS photodiode array detector (or Agilent G4212A).
(3) eluents: A: $H_2O$+0.04% TFA, B: $CH_3CN$; gradient: 5% B→95% B (0.0 min-1.0 min), 95% B (1.0 min-1.5 min), flow: 4.5 mL/min; detection: UV/Vis+MS, $t_R$ is given in min; column: Waters XBridge C18, 2.5 um, 4.6×30 mm.
(4) eluents: A: $H_2O$+0.04% TFA, B: $CH_3CN$; gradient: 2% B→40% B (0.0 min-0.8 min), 40% B→95% B (0.8 min-1.2 min), 95% B (1.2 min-1.5 min); flow: 4.5 mL/min; detection: UV/Vis+MS, $t_R$ is given in min; column: Waters XBridge O18, 2.5 um, 4.6×30 mm.
Purification Methods Used
Preparative LC-MS Methods:
Preparative HPLC/MS purifications were performed on a Waters system, equipped with a binary gradient module (2545), a HPLC pump (515), a photodiode array detector (2998) and a mass detector (3100).
eluents acidic: A: $H_2O$+0.1% HCOOH, B: $CH_3CN$+0.1% HCOOH; eluents basic: A: $H_2O$+01% $NH_4OH$, B: $CH_3CN$+0.1% $NH_4OH$; flow: 40 mL/min; column: Waters XBridge C18, 5 um OBD™, 19×50 mm.
normal gradient: 75% A (0.0 min-0.2 min), 75% A→65% A (0.2 min-0.3 min), 65% A→35% A (0.3 min-3.2 min), 35% A 5% A (3.2 min-3.3 min), 5% A (3.3 min-4.3 min).
polar gradient: 90% A (0.0 min-0.2 min), 90% A→80% A (0.2 min-0.3 min), 80% A→50% A (03 min-3.2 min), 50% A→5% A (3.2 min-3.3 min), 5% A (33 min-4.3 min).

very polar gradient: 95% A (0.0 min-0.3 min), 95% A→65% A (0.3 min-3.2 min), 65% A→5% A (3.2 min-3.3 min), 5% A (3.3 min-4 min).

|  | acidic | basic |
|---|---|---|
| very polar gradient | (A) | — |
| polar gradient | (B) | (D) |
| normal gradient | | (C) |

Preparative HPLC/MS purifications were performed on a Gilson HPLC system, equipped with a Gilson 215 autosampler, Gilson 333/334 pumps, Dionex MSQ Plus detector system, and a Dionex UVD340U (or Dionex DAD-3000) UV detector.

Method (E): eluents: A: $CH_3CN$, B: $H_2O$+0.5% HCOOH; gradient: 80% B→5% B (0.0 min-4.0 min), 5% B (4.0 min-6.0 min); flow: 75 mL/min; column: Waters XBridge C18, 10 urn, 30×75 mm.

Method (F): eluents: A: $CH_3CN$, B: $H_2O$+0.5% $NH_4OH$; gradient: 80% B→5% B (0.0 min-4.0 min), 5% B (4.0 min-6.0 min); flow: 75 mL/min; column: Waters XBridge C18, 10 um, 30×75 mm.

Method (G): eluents: A: $CH_3CN$, B: $H_2O$+0.5% HCOOH; gradient: 100% B (0.0 min-1.0 min), 100% B→80% B (1.0 min-3.5 min), 80% B→5% B (3.5 min-4.0 min), 5% B (4.0 min-6.0 min); flow: 75 mL/min; column: Waters Atlantis T3 OBD, 10 um, 30×75 mm.

Racemates can be separated into their enantiomers by preparative chiral HPLC.

The following examples illustrate the invention but do not at all limit the scope thereof.

A. Preparation of Precursors and Intermediates

A.1. Synthesis of Carboxylic Acid Derivatives (II)

A.1.1. Synthesis of 4,5,6,7-tetrahydrobenzo[d]thiazole-7-carboxylic acid

A.1.1.1. Methyl 2-bromo-3-oxocyclohexanecarboxylate

At 0° C., NBS (9.08 g, 51.0 mmol) was added to a soln. of methyl cyclohex-2-enecarboxylate (5.96 g, 42.5 mmol) [Bioorg. Med. Chem. 1999, 7, 1505-1511.] in THF/$H_2O$ (500 mL, 9:1). The mixture was allowed to warm to RT and stirred for 2 h. Subsequently, aq. sat. $Na_2S_2O_3$ and aq. sat. $NaHCO_3$ were added and the mixture was conc. in vacuo. The residue was partitioned between EtOAc and aq. sat. $NaHCO_3$. The org. layer was washed multiple times with aq. sat. $NaHCO_3$ and brine, dried over $MgSO_4$, and conc. in vacuo.

The residue was dissolved in DCM (386 mL) and DMP (24.54 g, 57.9 mmol) was added at 0° C. The mixture was allowed to warm to RT and stirred for 2 h. Subsequently, the mixture was quenched by the addition of aq. sat. $Na_2S_2O_3$ and aq. sat. $NaHCO_3$, diluted with $H_2O$, and extracted with DCM. The comb. org. layers were washed with brine, dried over $MgSO_4$, and conc. in vacuo. Purification by means of CC (0-0.5% MeOH/DCM) provided a yellow oil.

$^1$H-NMR ($CDCl_3$) δ: 4.75 (dd, J=6.7, 1.0 Hz, 0.2H), 4.65 (d, J=3.7 Hz, 0.8 Hz), 3.75, 3.75 (2 s, 3H), 3.16-3.01, 2.85-2.79, 2.47-2.39, 2.35-2.29 (4 m, 3H), 2.28-1.95, 1.88-1.79, 1.72-1.59 (3 m, 4H).

A.1.1.2. Methyl 4,5,6,7-tetrahydrobenzo[d]thiazole-7-carboxylate

At 0° C., finely crushed $P_4S_{10}$ (9.35 g, 21.0 mmol) was added to a mixture of formamide (4.73 g, 105.0 mmol) in dioxane (28.5 mL). Subsequently, the mixture was stirred in a sealed vial at 100° C. for 1.5 h, cooled to RT and filtrated. The filtrate was added to a mixture of methyl 2-bromo-3-oxocyclohexanecarboxylate (2.06 g, 8.76 mmol) in dioxane (16.5 mL) and stirred in a sealed vial at 80° C. overnight. The mixture was quenched by the addition of aq. sat. $NaHCO_3$ and extracted with EtOAc. The comb. org. layers were washed with brine, dried over $MgSO_4$, and conc. in vacuo. Purification by means of CC (10-40% EtOAc/Hept) provided a yellow oil.

LC-MS (3): $t_R$=0.47 min; [M+H]+: 198.16.

A.1.1.3. 4,5,6,7-Tetrahydrobenzo[d]thiazole-7-carboxylic acid

A mixture of methyl 4,5,6,7-tetrahydrobenzo[d]thiazole-7-carboxylate (1.22 g, 6.11 mmol) and LiOH.$H_2O$ (0.39 g, 9.17 mmol) in THF/MeOH/$H_2O$ (60 mL, 3:1:1) was stirred at RT for 75 min. The mixture was acidified to pH=3 and extracted with DCM. The comb. org. layers were dried over $MgSO_4$ and conc. in vacuo to provide a yellow solid.

LC-MS (3): $t_R$=0.32 min; [M+H]+: 184.21.

A.1.2. Synthesis of 5,6-dihydro-4H-cyclopenta[d]thiazole-6-carboxylic acid

A.1.2.1. 2-Bromo-3-oxocyclopentanecarbonitrile

Bicyclo[2.2.1]hepta-2,5-diene (0.84 g, 9.14 mmol), followed by Gd(OTf)$_3$ (1.84 g, 3.05 mmol), 2-cyclopenten-1-one (5.00 g, 60.9 mmol) and TMS-CN (9.25 g, 91.4 mmol) were added to a degassed solution of Ni(cod)$_2$ (0.84 g, 3.04 mmol) in THF (160 mL) and the mixture was stirred at RT for 4 h. Subsequently, the mixture was quenched with solid $NaHCO_3$ and aq. sat. $NaHCO_3$ and extracted with EtOAc. The comb. org. layers were washed with brine, dried over $MgSO_4$ and conc. in vacuo. The residue, a yellow oil, was dissolved in THF/$H_2O$ (450 mL, 9:1). At 0° C., NBS (11.98 g, 67.3 mmol) was added and the mixture was stirred at 0° C. for 30 min. Subsequently, the mixture was quenched with aq. sat. $Na_2SO_3$ and extracted with EtOAc. The comb. org. layers were washed with aq. 5% $NaHCO_3$ and brine, dried over $Na_2SO_4$, and conc. in vacuo. The residue was re-dissolved in EtOAc, washed multiple times with aq. 5% $NaHCO_3$ and brine, the combined org. layer were dried over $Na_2SO_4$, and conc. in vacuo to provide a brown liquid.

$^1$H-NMR ($CDCl_3$) δ: 4.42 (d, J=7.7 Hz, 0.5H), 4.34 (d, J=5.8 Hz, 0.5H), 3.43-3.40 (m, 0.5H), 3.33-3.28 (m, 0.5H), 2.72-2.26 (m, 4H).

A.1.2.2. 2-Amino-5,6-dihydro-4H-cyclopenta[d]thiazole-6-carbonitrile

A mixture of 2-bromo-3-oxocyclopentanecarbonitrile (crude from A.1.2.1.; ca. 13 g) and thiourea (13.77 g, 181 mmol) in dioxane (600 mL) was stirred at 80° C. for 1 h. The mixture was allowed to cool to RT, quenched with aq. sat. $NaHCO_3$ and extracted with EtOAc. The comb. org. layers were washed with brine, dried over $MgSO_4$, and conc. in vacuo. Purification by means of CC (2-20% MeOH (0.5% Et₃N)/DCM) provided a brown solid.
LC-MS (3): $t_R$=0.19 min; [M+H]+: 166.06.

A.1.2.3. 5,6-Dihydro-4H-cyclopenta[d]thiazole-6-carbonitrile

To a soln. of 2-amino-5,6-dihydro-4H-cyclopenta[d]thiazole-6-carbonitrile (1.00 g, 6.05 mmol) in THF (54 mL) was added tert-butyl nitrite (1.04 g, 9.08 mmol) and the mixture was stirred at 65° C. for 3 h. Subsequently, the mixture was quenched with aq. sat. NaHCO₃ and extracted with EtOAc. The comb. org. layers were washed with brine, dried over MgSO₄, and conc. in vacuo. Purification by means of CC (10-80% EtOAc/Hept) provided a yellow oil.
LC-MS (4): $t_R$=0.52 min; [M+H]+: 151.13.

A.1.2.4. 5,6-Dihydro-4H-cyclopenta[d]thiazole-6-carboxylic acid

A soln. of 5,6-dihydro-4H-cyclopenta[d]thiazole-6-carbonitrile (265 mg, 1.59 mmol) in aq. conc. HCl was stirred at 90° C. for 45 min in a sealed tube. The mixture was adjusted to pH=3 and extracted with EtOAc. The comb. org. layers were washed with brine, dried over MgSO₄, and conc. in vacuo to provide a yellow oil.
LC-MS (3): $t_R$=0.33 min; [M+H]+: 170.03.

A.1.3. Synthesis of 5,6,7,8-tetrahydro-4H-cyclohepta[d]thiazole-8-carboxylic acid

A.1.3.1. 2-Amino-5,6,7,8-tetrahydro-4H-cyclohepta[d]thiazole-8-carbonitrile

Bicyclo[2.2.1]hepta-2,5-diene (0.50 g, 5.45 mmol), followed by Gd(OTf)₃ (1.10 g, 1.82 mmol), 2-cyclohepten-1-one (5.00 g, 36.3 mmol) and TMS-CN (5.51 g, 54.5 mmol) were added to a degassed solution of Ni(cod)₂ (0.50 g, 1.82 mmol) in THF (100 mL) and the mixture was stirred at RT for 4 h. Subsequently, the mixture was quenched with solid NaHCO₃ and aq. sat. NaHCO₃ and extracted with EtOAc. The comb. org. layers were washed with brine, dried over MgSO₄ and conc. in vacuo.

The residue, a yellow oil, was dissolved in THF/H₂O (200 mL, 9:1). At 0° C., NBS (5.53 g, 31.0 mmol) was added and the mixture was stirred at 0° C. for 30 min. Subsequently, the mixture was quenched with aq. sat. Na₂SO₃ and extracted with EtOAc. The comb. org. layers were washed with aq. 5% NaHCO₃ and brine, dried over Na₂SO₄, and conc. in vacuo. The residue was re-dissolved in EtOAc, washed multiple times with aq. 5% NaHCO₃ and brine, the combined org. layer were dried over Na₂SO₄, conc. in vacuo and the residue was filtrated over a plug of SiO₂ with EtOAc/Hept (1:1) as eluent.

After conc. in vacuo, the residue, a brown oil, and thiourea (6.34 g, 83.2 mmol) were dissolved in dioxane (330 mL) and the mixture was stirred at 80° C. for 2 h. Subsequently, the mixture was quenched with aq. sat. NaHCO₃ and extracted with EtOAc. The comb. org. layers were washed with brine, dried over MgSO₄, and conc. in vacuo. Purification by means of CC (2-20% MeOH/DCM) provided a brown oil.
LC-MS (3): $t_R$=0.34 min; [M+H]+: 194.21.

A.1.3.2. 5,6,7,8-Tetrahydro-4H-cyclohepta[d]thiazole-8-carbonitrile

To a soln. of 2-amino-5,6,7,8-tetrahydro-4H-cyclohepta[d]thiazole-8-carbonitrile (1.00 g, 5.17 mmol) in THF (46 mL) was added tert-butyl nitrite (0.65 g, 5.68 mmol) and the mixture was stirred at 65° C. for 2.5 h. Subsequently, the mixture was quenched with aq. sat. NaHCO₃ and extracted with EtOAc. The comb. org. layers were washed with brine, dried over MgSO₄, and conc. in vacuo. Purification by means of CC (2-40% EtOAc/Hept), CC (0-1.5% MeOH/DCM) and prep. HPLC (E) provided a yellow oil.
LC-MS (3): $t_R$=0.51 min; [M+H]+: 179.23.

A.1.3.3. 5,6,7,8-Tetrahydro-4H-cyclohepta[d]thiazole-8-carboxylic acid

A soln. of 5,6,7,8-tetrahydro-4H-cyclohepta[d]thiazole-8-carbonitrile (151 mg, 0.84 mmol) in aq. conc. HCl (2 mL) was stirred at 90° C. for 1 h in a sealed tube. The mixture was adjusted to pH=3 and extracted with EtOAc. The combined org. layers were washed with brine, dried over MgSO₄, and conc. in vacuo to provide a beige solid.
LC-MS (3): $t_R$=0.36 min; [M+H]+: 198.20.

A.1.4. Synthesis of 6,7-dihydro-5H-pyrano[2,3-d]thiazole-7-carboxylic acid

A.1.4.1. 3-((tert-Butyldimethylsilyl)oxy)-1-(2,4-dichlorothiazol-5-yl)propan-1-01

At -20° C., a soln. of n-BuLi in hexanes (2.3 M, 10.9 mL, 25.0 mmol) was added to a soln. of DIPA (3.5 mL, 25.0 mmol) in THF (102 mL). The soln. was stirred at -20° C. for 30 min, then, it was cooled to -78° C. and a soln. of 2,4-dichlorothiazole (3.50 g, 22.7 mmol) in THF (16 mL) was added. The mixture was stirred at -78° C. for 30 min, then, 3-[(tert-butyldimethylsilyl)oxy]-1-propanal (4.51 g, 22.7 mmol) was added and the mixture was stirred at -78° C. for 1 h. Subsequently, the mixture was quenched with aq. sat. NH₄Cl and extracted with EtOAc. The comb. org. layers were washed with brine, dried over MgSO₄, and conc. in vacuo. Purification by means of CC (2-15% EtOAc/Hept) provided a yellow oil. LC-MS (3): $t_R$=1.08 min; [M+H]+: 342.08.

A.1.4.2. 5-(3-((tert-Butyldimethylsilyl)oxy)-1-((tetrahydro-2H-pyran-2-yl)oxy)propyl)-2,4-dichlorothiazole A soln. of 3-((tert-butyldimethylsilyl)oxy)-1-(2,4-dichlorothiazol-5-yl)propan-1-01 (6.62 g, 19.3 mmol), 3,4-dihydro-2H-pyran (8.9 mL, 96.7 mmol) and PPTS (0.49 g, 1.93 mmol) in DCM (75 mL) was stirred under reflux for 2 h. Subsequently, the volatiles were removed in vacuo and the residue was purified by means of CC (1-10% EtOAc/Hept) to provide the product as a colorless oil as an isomeric mixture.
LC-MS (3): $t_R$=1.27 min; 1.28 min; [M+H]+: 426.11; 426.10.

A.1.4.3. 5-(3-((tert-Butyldimethylsilyl)oxy)-1-((tetrahydro-2H-pyran-2-yl)oxy)propyl)-4-chlorothiazole At -78° C., a soln. of n-BuLi in hexanes (2.2 M, 9.6 mL, 21.0 mmol) was added to a soln. of 5-(3-((tert-butyldimethylsilyl)oxy)-1-((tetrahydro-2H-pyran-2-yl)oxy)propyl)-2,4-dichlorothiazole (6.89 g, 16.2 mmol) in THF (125 mL). The mixture was stirred at -78° C. for 45 min, then, quenched by the addition of aq. sat. NaHCO₃ and extracted with EtOAc. The comb. org. layers were washed with brine, dried over MgSO$_4$, and conc. in vacuo. Purification by means of CC (2-20% EtOAc/Hept) provided the product as a yellow oil as an isomeric mixture.

LC-MS (3): t$_R$=1.15 min; 1.16 min; [M+H]+: 392.17; 392.17.

A.1.4.4. 3-(4-Chlorothiazol-5-yl)-3-((tetrahydro-2H-pyran-2-yl)oxy)propan-1-ol At 0° C., a soln. of TBAF in THF (1 M, 19.2 mL, 19.2 mmol) was added to a. soln. of 5-(3-((tert-butyldimethylsilyl)oxy)-1-((tetrahydro-2H-pyran-2-yl)oxy)propyl)-4-chlorothiazole (6.27 g, 16.0 mmol) in THF (80 mL). The mixture was allowed to warm to RT and stirred overnight. Then, the mixture was quenched by the addition of aq. sat. NaHCO$_3$ and extracted with EtOAc. The comb. org. layers were washed with brine, dried over MgSO$_4$, and conc. in vacuo. Purification by means of CC (20-85% EtOAc/Hept) provided the product as a yellow oil as an isomeric mixture.

LC-MS (3): t$_R$=0.55 min; 0.57 min; [M+H]+: 278.11; 278.10.

A.1.4.5. 7-((Tetrahydro-2H-pyran-2-yl)oxy)-6,7-dihydro-5H-pyrano[2,3-d]thiazole A soln. of 3-(4-chlorothiazol-5-yl)-3-((tetrahydro-2H-pyran-2-yl)oxy)propan-1-ol (520 mg, 1.87 mmol) in MePh (10 mL) was added to a Ar-filled vial charged with Pd(OAc)$_2$ (63 mg, 0.28 mmol), 2-(di-tert-butylphosphino)-1,1'-binaphthyl (140 mg, 0.35 mmol) and Cs$_2$CO$_3$ (915 mg, 2.81 mmol). The vial was sealed and placed in a preheated oilbath (100° C.) overnight. Subsequently, the mixture was diluted with DCM, filtrated over Celite, and conc. in vacuo. Purification by means of CC (20-80% EtOAc/Hept) provided the product as a yellow oil as an isomeric mixture.

LC-MS (3): t$_R$=0.60 min; 0.64 min; [M+H]+: 241.94; 241.94.

A.1.4.6. 6,7-Dihydro-5H-pyrano[2,3-d]thiazol-7-ol

A soln. of 7-((tetrahydro-2H-pyran-2-yl)oxy)-6,7-dihydro-5H-pyrano[2,3-d]thiazole (895 mg, 3.71 mmol) and PTSA (141 mg, 0.74 mmol) in THF/H$_2$O (7.4 mL, 1:1) was stirred at RT overnight. The mixture was diluted with DCM, dried over Na$_2$SO$_4$, and conc. in vacuo. Purification by means of CC (40-100% EtOAc/Hept) provided a yellow oil.

LC-MS (3): t$_R$=0.23 min; [M+H]+: 158.15.

A.1.4.7. 6,7-Dihydro-5H-pyrano[2,3-d]thiazole-7-carbonitrile

To a mixture of 6,7-dihydro-5H-pyrano[2,3-d]thiazol-7-ol (0.65 g, 4.14 mmol), acetone cyanohydrin (880 mg, 10.3 mmol) and (n-Bu)$_3$P (1.67 g, 8.27 mmol) in THF (79 mL) was added at 0° C. 1,1'-(azodicarbonyl)dipiperidine (2.09 g, 8.27 mmol). The mixture was stirred at 0° C. for 30 min, then, it was allowed to warm to RT and was stirred for 2 h. Subsequently, the reaction mixture was diluted with diisopropyl ether, filtrated and the filtrate was conc. in vacuo. Purification by means of CC (5-70% EtOAc/Hept) provided a yellow solid.

LC-MS (3): t$_R$=0.36 min; [M+H]+: 167.13.

A.1.4.8. 6,7-Dihydro-5H-pyrano[2,3-d]thiazole-7-carboxylic acid

A soln. of 6,7-dihydro-5H-pyrano[2,3-d]thiazole-7-carbonitrile (462 mg, 2.78 mmol) in aq. HCl (32%, 13.9 mL) was stirred at 60° C. for 30 min. Under ice-bath cooling, the pH of the mixture was adjusted to ca. 3, and the mixture was extracted with EtOAc. The comb. org. layers were dried over MgSO$_4$ and conc. in vacuo to provide a beige solid.

LC-MS (3): t$_R$=0.33 min; [M+H]+: 186.18.

A.1.5. Synthesis of 5,6-dihydrofuro[2,3-d]thiazole-6-carboxylic acid

A.1.5.1. 4-((2,2-Dimethyl-1,3-dioxolan-4-yl)methoxy)thiazole

NaH (60% dispersion in mineral oil, 12.19 g, 305.3 mmol) was added portionwise to DL-1,2-isopropylideneglycerol (16.11 g, 1218 mmol) and the mixture was stirred until gas evolution had ceased (ca. 30 min RT, followed by 2 h at 60° C.). Subsequently, 4-bromothiazole (20.00 g, 121.9 mmol) was added and the mixture was stirred at 140° C. for 45 min. Subsequently, the reaction mixture was quenched with aq. sat. NH$_4$Cl and extracted with EtOAc. The comb. org. layers were washed with brine, dried over MgSO$_4$, and conc. in vacuo. The residue was subjected to distillation and the volatiles (HV, 60° C.) were removed. The residue was purified by means of CC (5-40% EtOAc/Hept) to provide a yellow oil.

LC-MS (3): t$_R$=0.52 min; [M+H]+: 216.20.

A.1.5.2. 5-Bromo-4-((2,2-dimethyl-1,3-dioxolan-4-yl)methoxy)thiazole

At 0° C., NBS (11.94 g, 67.1 mmol) was added over 90 min to a soln. of 4-((2,2-dimethyl-1,3-dioxolan-4-yl)methoxy)thiazole (13.75 g, 63.9 mmol) in MeCN (320 mL). The mixture was further stirred at 0° C. for 30 min, then, it was quenched by the addition of aq. 5% NaHCO$_3$ and extracted with EtOAc. The comb. org. layers were washed with aq. 5% NaHCO$_3$ and brine, dried over MgSO$_4$, and conc. in vacuo.

LC-MS (3): t$_R$=0.74 min; [M+H]+: 294.13.

A.1.5.3. 5-Bromo-4-(oxiran-2-ylmethoxy)thiazole

A soln. of 5-bromo-4-((2,2-dimethyl-1,3-dioxolan-4-yl)methoxy)thiazole (18.80 g, 63.9 mmol) and PPTS (0.80 g, 3.19 mmol) in MeOH (256 mL) was stirred under reflux for 3 h. More PPTS (0.40 g, 1.60 mmol) was added and the mixture was stirred under reflux for additional 2 h. The mixture was conc. in vacuo, the residue was dissolved in MeOH (256 mL) and stirred under reflux for 2 h. The mixture was conc. in vacuo, the residue was dissolved in DCM (256 mL) and treated with trimethyl orthoformate (10.5 mL, 95.8 mmol). The mixture was stirred overnight at RT. Subsequently, additional trimethyl orthoformate (3.5 mL, 31.9 mmol) was added and the mixture was stirred at RT for 1 h. Then, the mixture was conc. in vacuo, the residue was dissolved in DCM (256 mL), treated with AcBr (5.73 mL, 76.7 mmol) and stirred at RT for 90 min. Subsequently, the mixture was conc. in vacuo, the residue was dissolved in MeOH (320 mL) and K$_2$CO$_3$ (17.66 g, 128 mmol) was added to the mixture. After the mixture was stirred at RT for 90 min, the mixture was filtrated and the filtrate was poured into cold aq. sat. NH$_4$Cl. The mixture was extracted with EtOAc, the comb. org. layers were washed with brine, dried over MgSO$_4$, and conc. in vacuo. The residue was purified by means of CC (2-40% EtOAc/Hept) to provide a yellow oil.

LC-MS (3): t$_R$=0.60 min; [M+H]+: 236.06.

A.1.5.4. (2-(Triisopropylsilyl)-5,6-dihydrofuro[2,3-d]thiazol-6-yl)methanol At −78° C., a soln. of n-BuLi in hexanes (2.18 M, 16.7 mL, 36.4 mmol) was added over 30 min to a soln. of 5-bromo-4-

(oxiran-2-ylmethoxy)thiazole (7.17 g, 30.4 mmol) in THF (564 mL). The mixture was stirred at −78° C. for 2 h, then, TIPSCl (6.63 mL, 31.0 mmol) was added, the mixture was allowed to warm to RT and stirred at RT for 30 min. Subsequently, the mixture was cooled to −78° C. and treated with a soln. of n-BuLi in hexanes (2.18 M, 13.9 mL, 30.4 mmol). The mixture was stirred at 0° C. for 2 h, then, it was quenched with aq. sat. NaHCO$_3$ and extracted with EtOAc. The comb. org. layers were washed with brine, dried over MgSO$_4$, and conc. in vacuo. The residue was purified by means of CC (5-50% EtOAc/Hept) to provide a yellow oil.

LC-MS (3): $t_R$=1.01 min; [M+H]+: 314.13.

A.1.5.5. 2-(Triisopropylsilyl)-5,6-dihydrofuro[2,3-d]thiazole-6-carboxylic acid A soln. of (2-(triisopropylsilyl)-5,6-dihydrofuro[2,3-d]thiazol-6-yl)methanol (1.77 g, 5.64 mmol)) in DCM (56 mL) was treated at 0° C. with DMP (2.87 g, 6.77 mmol) portionwise over 1 h. The mixture was stirred at 0° C. for 2 h, then, it was allowed to warm to RT and stirred for 2 h. Subsequently, the mixture was quenched with aq. sat. Na$_2$S$_2$O$_3$ and aq. sat. NaHCO$_3$ and was extracted with DCM. The comb. org. layers were washed with brine, dried over MgSO$_4$, and conc. in vacuo. The residue was dissolved in tert-BuOH (16 mL) and 2-methyl-2-butene (4 mL) and treated at 0° C. dropwise over 30 min with a soln. of NaH$_2$PO$_4$ (2.64 g, 16.9 mmol) and NaClO$_2$ (0.96 g, 8.46 mmol) in H$_2$O (5 mL). The mixture was stirred at RT for 45 min, then, the volatiles were removed in vacuo, the residue was diluted with H$_2$O and extracted with EtOAc. The comb. org. layers were dried over MgSO$_4$ and conc. in vacuo.

LC-MS (3): $t_R$=0.99 min; [M+H]+: 328.24.

A.1.5.6. 5,6-Dihydrofuro[2,3-d]thiazole-6-carboxylic acid

A soln. of TBAF in THF (1 M, 4.9 mL, 4.90 mmol) was added at 0° C. to soln. of 2-(triisopropylsilyl)-5,6-dihydrofuro[2,3-d]thiazole-6-carboxylic acid (1.62 mg, 4.90 mmol) in THF (25 mL). The mixture was stirred at 0° C. for 30 min, AcOH (0.42 mL, 7.35 mmol) was added, and the volatiles were removed in vacuo. The residue was purified by means of prep. HPLC (G) to provide a colorless solid.

LC-MS (3): $t_R$=0.30 min; [M+H]+: 172.05.

A.2. Synthesis of Amines (III)

A.2.1. Synthesis of 2-amino-2-cycloheptylethanol

A.2.1.1. Synthesis of 2-amino-2-cycloheptylacetic acid tert-butyl ester

To a soln. of N-(diphenylmethylene)glycerine tert-butyl ester (6.83 mmol) and (R)-4,4-dibutyl-2,6-bis(3,4,5-trifluorophenyl)-4,5-dihydro-3H-dinaphthol[7,6,1,2-cde]azepinium bromide (6.84 µmol) in 45 mL toluene were sequentially added cycloheptyl bromide (8.2 mmol) and CsOH H$_2$O (34.2 mmol) at −10° C. The reaction mixture was stirred at −10° C. for 10 min and then at RT for 4 days. Another portion of (R)-4,4-dibutyl-2,6-bis(3,4,5-trifluorophenyl)-4,5-dihydro-3H-dinaphthol[7,6,1,2-cde]azepinium bromide (6.84 µmol) was added and stirring was continued at RT for another 24 h. The reaction was quenched with water and extracted 3 times with DCM. The comb. org. layers were combined, conc. and the residue was redissolved in 100 mL THF. A soln. of 100 mL aq. 0.5 M citric acid soln. was added and the mixture was stirred at RT for 4 h. The mixture was concentrated to half of its volume and extracted twice with Et$_2$O. The aqueous layer was basified with solid NaHCO$_3$ and extracted 3 times with DCM. The comb. org. layers were dried over MgSO$_4$ and conc. in vacuo to obtain the desired product as yellow oil.

LC-MS (3): $t_R$=0.61 min; [M+H]+: 228.29.

A.2.1.2 Synthesis of 2-amino-2-cycloheptylethanol

To a soln. of 3.43 mL LiAlH$_4$ (1 M in THF) in 8 mL THF was added a soln. of 2-amino-2-cycloheptylacetic acid tert-butyl ester (1.72 mmol) in 3 mL THF at 0° C. The ice bath was removed and stirring was continued at RT for 1 h. The reaction mixture was cooled to 0° C., quenched with water and a 1 M NaOH soln., filtered over a pad of celite and washed with EtOAc. The filtrate was basified with a 1 M NaOH soln. to pH 8-9 and it was then extracted 3 times with EtOAc. The comb. org. layers were dried over MgSO$_4$ and conc. in vacuo to obtain the crude product as yellow oil. The crude was dissolved in 3 mL Et$_2$O and a soln. of 4 M HCl in dioxane was dropwise added at 0° C. The resulting precipitate was separated by filtration and dried in vacuo to give the corresponding HCl salt as yellow solid.

LC-MS (3): $t_R$=0.39 min; [M+H]+: 158.14.

A.2.2. Synthesis of (1-(6-chloropyridin-3-yl)cyclohexyl)methanamine

A.2.2.1. Synthesis of 1-(6-chloropyridin-3-yl)cyclohexanecarbonitrile

To a mixture of 2-(6-chloropyridin-3-yl)acetonitrile (26.2 mmol) and 1,5-dibromopentane (26.2 mmol) in THF/DMSO (1:1, 300 mL) was added NaH (60% in mineral oil, 55.1 mmol) portionwise at 0° C. over 45 min. The mixture was allowed to warm to RT and stirred for 1 h 45 min. The reaction mixture was poured into water and extracted with DCM. The comb. org. layers were washed with brine, dried over MgSO$_4$, and conc. in vacuo. The residue was purified by means of CC (10-80% EtOAc/Hept) to provide a colorless solid.

LC-MS (3): $t_R$=0.78 min; [M+H]+: 221.20.

A.2.2.2. Synthesis of (1-(6-chloropyridin-3-yl)cyclohexyl)methanamine

A soln. of 1-(6-chloropyridin-3-yl)cyclohexanecarbonitrile (20.1 mmol) in THF (88 mL) was added dropwised to a solution BH$_3$ in THF (60.2 mmol, 1 M). After heating to reflux for 1 h, the reaction mixture was cooled in an ice bath before aq. 2 M HCl (120 mL) was slowly added. The mixture was then heated to reflux for another 20 min. After cooling to RT, the mixture was washed with DCM, then, it was basified with aq. 1 M NaOH and extracted with DCM. The comb. org. layers were dried over MgSO$_4$ and conc. in vacuo.

LC-MS (3): $t_R$=0.47 min; [M+H]+: 225.27.

A.2.3. Synthesis of (1-(6-chloropyridin-3-yl)-4,4-difluorocyclohexyl)methanamine

A.2.3.1. Synthesis of methyl 5-(6-chloropyridin-3-yl)-5-cyano-2-hydroxycyclohex-1-enecarboxylate To a soln. of 2-(6-chloro-3-pyridinyl)acetonitrile (13.1 mmol) in 35 mL THF were added methylacrylate (26.2 mmol) and KOtBu (15.7 mmol). The reaction mixture was stirred at RT for 1 h. The mixture was acidified with aq. 1 M HCl soln. and then extracted with DCM. The comb. org. layers were washed with brine, dried over MgSO$_4$ and conc. in vacuo. The residue was purified by CC (10-50% EtOA/Hept) to provide a white solid.

LC-MS (3): t$_R$=0.74 min; [M+CH$_3$CN+H]+: 334.03.

A.2.3.2. Synthesis of 1-(6-chloropyridin-3-yl)-4-oxocyclohexanecarbonitrile

A mixture of methyl 5-(6-chloropyridin-3-yl)-5-cyano-2-hydroxycyclohex-1-enecarboxylate (10.6 mmol) and LiCl (21.1 mmol) in 15 mL wet DMSO was heated to 120° C. under microwave conditions for 2 h. The reaction mixture was diluted with water and extracted with EtOAc. The comb. org. layers were washed with brine, dried over MgSO$_4$ and conc. in vacuo. The residue was purified by CC (5-20% EtOAc/Hept) to provide a yellow solid.

LC-MS (3): t$_R$=0.56 min; [M+CH$_3$CN+H]+: 276.12.

A.2.3.3. Synthesis of 1-(6-chloropyridin-3-yl)-4,4-difluorocyclohexanecarbonitrile A soln. of 1-(6-chloropyridin-3-yl)-4-oxocyclohexanecarbonitrile (3.89 mmol) in 4 mL DCM was cooled to −78° C., (diethylamino)sulfur trifluoride (7.78 mmol) was dropwise added and the mixture was stirred for 24 h allowing to reach slowly RT. The reaction mixture was quenched with aq. sat. NaHCO$_3$ solution under ice cooling and diluted with DCM. The org. phase was washed with brine, dried over MgSO$_4$ and conc. in vacuo. The residue was purified by CC (10-50% EtOAc/Hept) to provide a beige solid.

LC-MS (3): t$_R$=0.74 min; [M+CH$_3$CN+H]+: 298.00.

A.2.3.4. Synthesis of (4,4-difluoro-1-(6-chloropyridin-3-yl)cyclohexyl)methanamine A soln. of 1-(6-chloropyridin-3-yl)-4,4-difluorocyclohexanecarbonitrile (2.02 mmol) in 20 mL THF was added to a soln. of BH$_3$ in THF (6.07 mmol, 1 M). After heating to reflux for 1 h, the reaction mixture was cooled in an ice bath before a 2 M HCl soln. was slowly added. The mixture was then heated to reflux for another 20 min. The reaction mixture was washed with DCM, basified with aq. 1 M NaOH and extracted with DCM. The com. org. layers were washed with brine, dried over MgSO$_4$ and conc. in vacuo to provide a yellow oil.

LC-MS (3): t$_R$=0.46 min; [M+CH$_3$CN+H]+: 302.03.

A.2.4. Synthesis of 2-alkyl-2-heteroarylethanamines

A.2.4.1. Strecker Reaction (General Procedure I)

To a suspension of the corresponding aldehyde (24.6 mmol) in anh. Et$_2$O (8 mL) was slowly added at RT, TMS-CN (27 mmol) followed by ZnI$_2$ (1.23 mmol). The mixture was cooled to 0° C. and a solution of the corresponding amine (24.6 mmol) in anh. MeOH (20 mL) was added dropwise (when the amine was a HCl salt, 24.6 mmol of TEA were additionally added). The mixture was heated at 70° C. for 1 to 6 h then cooled to RT. It was quenched with an aq. 10% Na$_2$CO$_3$ soln. and extracted 3 times with EtOAc. The comb. org. phases were dried over MgSO$_4$ and conc. in vacuo. The crude was purified by CC (KP-NH from Biotage) to isolate the desired α-amino-nitrile (see table below).

| Name | LC-MS type | tR (min) | [M + H]+ |
|---|---|---|---|
| 2-morpholino-2-(2-(trifluoromethyl)pyrimidin-5-yl)acetonitrile | 3 | 0.65 | [M + MeCN + H]+: 313.99 |
| 2-(6-chloropyridin-3-yl)-2-(4,4-difluoropiperidin-1-yl)acetonitrile | 3 | 0.76 | 272.25 |
| 2-(2-methylpyrimidin-5-yl)-2-morpholinoacetonitrile | 3 | 0.39 | 219.41 |
| 2-(4,4-difluoropiperidin-1-yl)-2-(2-methylpyrimidin-5-yl)acetonitrile | 3 | 0.59 | 253.05 |
| 2-morpholino-2-(6-(trifluoromethyl)pyridin-3-yl)acetonitrile | 3 | 0.68 | 272.01 |

A.2.4.2. Hydrogenation of Nitrile (General Procedure II)

To a soln. of the α-amino-nitrile (4.38 mmol) from the previous step in a 7 M solution of NH$_3$ in MeOH (32 mL) were added at 0° C. a 4% soln. of thiophene in diisopropylether (0.16 mL) and Actimet M Raney nickel. The mixture was allowed to warm to RT and stirred under a hydrogen atmosphere for 30 h. It was filtered over Celite, washed with MeOH and conc. in vacuo. The amine was optionally transformed to its HCl salt by dissolution in Et$_2$O (8.8 mL), addition of a 4 M HCl soln. in dioxane (4.4 mL) at 0° C. and filtration of the formed solid.

| Name | LC-MS type | tR (min) | [M + H]+ |
|---|---|---|---|
| 2-morpholino-2-(2-(trifluoromethyl)pyrimidin-5-yl)ethanamine | 3 | 0.40 | 277.09 |
| 2-(6-chloropyridin-3-yl)-2-(4,4-difluoropiperidin-1-yl)ethanamine | 3 | 0.50 | 276.30 |
| 2-(2-methylpyrimidin-5-yl)-2-morpholinoethanamine | 3 | 0.21 | 223.10 |
| 2-(4,4-difluoropiperidin-1-yl)-2-(2-methylpyrimidin-5-yl)ethanamine | 3 | 0.40 | 257.07 |
| 2-morpholino-2-(6-(trifluoromethyl)pyridin-3-yl)ethanamine | 3 | 0.41 | 276.10 |

B. Preparation of Examples

B.1. Synthesis of Compounds of Formula (I) (General Procedure)

A mixture of the respective carboxylic acid (II) (0.30 mmol), the respective amine (III) (0.36 mmol), HOBt (0.45 mmol), EDC.HCl (0.45 mmol) and DIPEA (0.90 mmol) in DMF (1.2 mL) was stirred at RT overnight. The mixture was filtrated and the filtrate was purified by purification methods listed beforehand to give the desired amides (I).

Example List

| Compound | Name | Purification method | LC-MS | $t_R$ [min] | $[M+H]^+$ |
|---|---|---|---|---|---|
| Example 1 | N-(1-cycloheptyl-2-hydroxyethyl)-5,6-dihydrofuro[2,3-d]thiazole-6-carboxamide (mixture of 4 isomers) | B | 1 | 0.83 | 311.0 |
| Example 2 | N-((1-(6-chloropyridin-3-yl)cyclohexyl)methyl)-5,6-dihydrofuro[2,3-d]thiazole-6-carboxamide | B | 1 | 1.04 | 378.0 |
| Example 3 | N-(2-(4,4-difluoropiperidin-1-yl)-2-(2-methylpyrimidin-5-yl)ethyl)-5,6-dihydrofuro[2,3-d]thiazole-6-carboxamide (mixture of 4 stereoisomers) | A | 1 | 0.59 | 410.0 |
| Example 4 | N-(2-morpholino-2-(6-(trifluoromethyl)pyridin-3-yl)ethyl)-5,6-dihydrofuro[2,3-d]thiazole-6-carboxamide (mixture of 4 stereoisomers) | A | 1 | 0.62 | 428.9 |
| Example 5 | N-((S)-1-cyclohexyl-2-hydroxyethyl)-5,6-dihydro-4H-cyclopenta[d]thiazole-6-carboxamide (mixture of epimers) | B | 1 | 0.76 | 295.2 |
| Example 6 | N-(2-(2-methylpyrimidin-5-yl)-2-morpholinoethyl)-5,6-dihydro-4H-cyclopenta[d]thiazole-6-carboxamide (mixture of 4 stereoisomers) | A | 1 | 0.32 | 373.8 |
| Example 7 | N-(2-(4,4-difluoropiperidin-1-yl)-2-(2-methylpyrimidin-5-yl)ethyl)-5,6-dihydro-4H-cyclopenta[d]thiazole-6-carboxamide (mixture of 4 stereoisomers) | A | 1 | 0.61 | 408.2 |
| Example 8 | N-((S)-1-cyclohexyl-2-hydroxyethyl)-6,7-dihydro-5H-pyrano[2,3-d]thiazole-7-carboxamide (mixture of epimers) | B | 1 | 0.74 | 310.9 |
| Example 9 | N-(2-(2-methylpyrimidin-5-yl)-2-morpholinoethyl)-6,7-dihydro-5H-pyrano[2,3-d]thiazole-7-carboxamide (mixture of 4 stereoisomers) | A | 1 | 0.31 | 389.7 |
| Example 10 | N-(2-(6-chloropyridin-3-yl)-2-(4,4-difluoropiperidin-1-yl)ethyl)-6,7-dihydro-5H-pyrano[2,3-d]thiazole-7-carboxamide (mixture of 4 stereoisomers) | B | 1 | 0.81 | 442.9 |
| Example 11 | N-((R)-1-cyclohexylethyl)-4,5,6,7-tetrahydrobenzo[d]thiazole-7-carboxamide (mixture of epimers) | C | 2 | 1.09 | 293.1 |
| Example 12 | N-((S)-1-cyclohexyl-2-hydroxyethyl)-4,5,6,7-tetrahydrobenzo[d]thiazole-7-carboxamide (mixture of epimers) | E, F | 3 | 0.53 | 309.0 |
| Example 13 | N-((1-(6-chloropyridin-3-yr)cyclohexyl)methyl)-4,5,6,7-tetrahydrobenzo[d]thiazole-7-carboxamide | C | 2 | 1.09 | 389.8 |
| Example 14 | N-((1-(6-chloropyridin-3-yl)-4,4-difluorocyclohexyl)methyl)-4,5,6,7-tetrahydrobenzo[d]thiazole-7-carboxamide | D | 2 | 0.99 | 426.1 |
| Example 15 | N-(2-morpholino-2-(2-(trifluoromethyl)pyrimidin-5-yl)ethyl)-4,5,6,7-tetrahydrobenzo[d]thiazole-7-carboxamide (mixture of 4 stereoisomers) | D | 2 | 0.80 | 442.1 |

-continued

| Compound | Name | Purification method | LC-MS | | |
| --- | --- | --- | --- | --- | --- |
| | | | LC-MS | $t_R$ [min] | $[M + H]^+$ |
| Example 16 | N-((S)-1-cyclohexyl-2-hydroxyethyl)-5,6,7,8-tetrahydro-4H-cyclohepta[d]thiazole-8-carboxamide (epimer A) | E | 3 | 0.56 | 323.2 |
| Example 17 | N-((S)-1-cyclohexyl-2-hydroxyethyl)-5,6,7,8-tetrahydro-4H-cyclohepta[d]thiazole-8-carboxamide (epimer B) | E | 3 | 0.53 | 323.0 |

Biological Assays
A. In Vitro Assay

The $P2X_7$ receptor antagonistic activity of the compounds of formula (I) is determined in accordance with the following experimental method.

B. Experimental Method:
Cell Line Generation and YO-PRO Assay

Cell line generation was performed in general according to established molecular cloning protocols. Specifically, RNA was extracted from human whole blood using the Qiagen RNeasy kit (Qiagen, CH) according to the manufacturer's instructions. Subsequently cDNA was made (Superscript II, Invitrogen AG, CH) and the human P2X7 gene (genbank ref. BC011913) was amplified with the following primers: ATCGCGGCCGCTCAGTAAGGACTCTTGAAGCCACT and CGCCGCTAGCACCACCATGCCGGCCT-GCTGCAGCTGCA. The amplified sequence was subsequently ligated into a pcDNA3.1 (+) NotI, NheI digested plasmid. Human embryonic kidney (HEK) cells (ATCC CRL-1573, Manassas, Va., USA) were transfected with the pcDNA3.1 (+). hP2X7 plasmid using lipofectamine 2000 (Invitrogen AG, CH) according to the manufacturer's instructions. Following a 24 h exposure to DNA, cells were trypsinized and re-seeded at low density in the presence of 250 µg Geneticin. Geneticin resistant cells were then selected during two consecutive rounds of cloning by serial limiting dilution with visual inspection. Individual clones were screened for P2X7 expression by applying ATP and recording the resultant uptake of YO-PRO1. Specific cell clones were chosen based on RNA and protein expression. HEK cells stably expressing P2X7 were used to screen drugs using the YO-PRO1 assay. Cells were grown to confluency in adherent culture at 37° C. in a humidified 5% $CO_2$ incubator (split 1/5 every 3-4 days with DMEM, 10% FCS, 1% Penicillin/Streptomycin, 250 µg/ml Geneticin).

Adherent cells were detached by incubation with Trypsine (1 ml per 165 $cm^2$ dish) for 2 minutes, then washed off with 10 ml PBS (without $Mg^{2+}$ and $Ca^{2+}$), and resuspended in DMEM, 10% FCS, 1% Penicillin/Streptomycin, no Geneticin. 10'000 cells per well (48 hours before the assay) or 25'000 cells per well (Vi-cell XR (Beckman Coulter) (24 hours before the assay) in 50 µl full medium were seeded on 384-well black-wall, clear bottom plates, that were coated before with 10 µl per well Poly-L-Lysine, incubated for 30-60 minutes at 37° C. and washed once with PBS. Medium was removed from cells and 50 µl of assay buffer containing 0.5 µMYO-PRO-1 was added into the wells. Solutions of antagonist compounds were prepared by serial dilutions of a 10 mM DMSO solution of the antagonist into PBS using a BioMek (Beckman Coulter). Each concentration was performed in duplicate. For $IC_{50}$ measurements 10 concentration points were measured (10 µM being the highest concentration followed by 9 serial dilution steps 1/3). The cells were incubated with the antagonists of the present invention together with ATP at a final concentration of 250 µM for 90 minutes. During this time period, four time points were taken. Each time point comprised the average of several measurements made within a few seconds. Fluorescence was measured in the FLIPR tetra (Molecular Devices) using the filters appropriate for YO-PRO-1 fluorescence (excitation 485/20, emission 530/25). The FLIPR tetra was equipped with Molecular Devices Screen Works system control software to define and run experimental protocols. For antagonist activity measurements, the maximal intensity was expressed as a percentage of that induced by the $EC_{50}$ value for agonist activation (0.25 mM ATP for HEK-293 cells expressing human recombinant P2X7 receptor). For IC50 measurements the maximum intensity is plotted against the concentration of compound to determine IC50 values.

Antagonistic activities with respect to the $P2X_7$ receptor ($IC_{50}$ values) of exemplified compounds are displayed in Table 1.

TABLE 1

| Compound | Name | $IC_{50}$ [nM] |
| --- | --- | --- |
| Example 1 | N-(1-cycloheptyl-2-hydroxyethyl)-5,6-dihydrofuro[2,3-d]thiazole-6-carboxamide (mixture of 4 stereoisomers) | 818 |
| Example 2 | N-((1-(6-chloropyridin-3-yl)cyclohexyl)methyl)-5,6-dihydrofuro[2,3-d]thiazole-6-carboxamide | 28 |
| Example 3 | N-(2-(4,4-difluoropiperidin-1-yl)-2-(2-methylpyrimidin-5-yl)ethyl)-5,6-dihydrofuro[2,3-d]thiazole-6-carboxamide (mixture of 4 stereoisomers) | 2035 |
| Example 4 | N-(2-morpholino-2-(6-(trifluoromethyl)pyridin-3-yl)ethyl)-5,6-dihydrofuro[2,3-d]thiazole-6-carboxamide (mixture of 4 stereoisomers) | 332 |

TABLE 1-continued

| Compound | Name | IC$_{50}$ [nM] |
|---|---|---|
| Example 5 | N-((S)-1-cyclohexyl-2-hydroxyethyl)-5,6-dihydro-4H-cyclopenta[d]thiazole-6-carboxamide (mixture of epimers) | 272 |
| Example 6 | N-(2-(2-methylpyrimidin-5-yl)-2-morpholinoethyl)-5,6-dihydro-4H-cyclopenta[d]thiazole-6-carboxamide (mixture of 4 stereoisomers) | 1372 |
| Example 7 | N-(2-(4,4-difluoropiperidin-1-yl)-2-(2-methylpyrimidin-5-yl)ethyl)-5,6-dihydro-4H-cyclopenta[d]thiazole-6-carboxamide (mixture of 4 stereoisomers) | 478 |
| Example 8 | N-((S)-1-cyclohexyl-2-hydroxyethyl)-6,7-dihydro-5H-pyrano[2,3-d]thiazole-7-carboxamide (mixture of epimers) | 340 |
| Example 9 | N-(2-(2-methylpyrimidin-5-yl)-2-morpholinoethyl)-6,7-dihydro-5H-pyrano[2,3-d]thiazole-7-carboxamide (mixture of 4 stereoisomers) | 1430 |
| Example 10 | N-(2-(6-chloropyridin-3-yl)-2-(4,4-difluoropiperidin-1-yl)ethyl)-6,7-dihydro-5H-pyrano[2,3-d]thiazole-7-carboxamide (mixture of 4 stereoisomers) | 74 |
| Example 11 | N-((R)-1-cyclohexylethyl)-4,5,6,7-tetrahydrobenzo[d]thiazole-7-carboxamide (mixture of epimers) | 60 |
| Example 12 | N-((S)-1-cyclohexyl-2-hydroxyethyl)-4,5,6,7-tetrahydrobenzo[d]thiazole-7-carboxamide (mixture of epimers) | 41 |
| Example 13 | N-((1-(6-chloropyridin-3-yl)cyclohexyl)methyl)-4,5,6,7-tetrahydrobenzo[d]thiazole-7-carboxamide | 3.4 |
| Example 14 | N-((1-(6-chloropyridin-3-yl)-4,4-difluorocyclohexyl)methyl)-4,5,6,7-tetrahydrobenzo[d]thiazole-7-carboxamide | 6.3 |
| Example 15 | N-(2-morpholino-2-(2-(trifluoromethyl)pyrimidin-5-yl)ethyl)-4,5,6,7-tetrahydrobenzo[d]thiazole-7-carboxamide (mixture of 4 stereoisomers) | 33 |
| Example 16 | N-((S)-1-cyclohexyl-2-hydroxyethyl)-5,6,7,8-tetrahydro-4H-cyclohepta[d]thiazole-8-carboxamide (epimer A) | 348 |
| Example 17 | N-((S)-1-cyclohexyl-2-hydroxyethyl)-5,6,7,8-tetrahydro-4H-cyclohepta[d]thiazole-8-carboxamide (epimer B) | 543 |

The invention claimed is:
1. A compound of the formula (I),

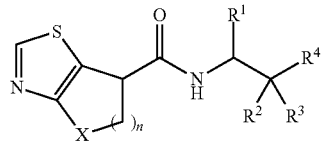

wherein
n represents 1, 2 or 3;
X represents —O— or —CH$_2$—;
R$^3$ represents hydrogen, (C$_1$-C$_2$)alkyl or hydroxy-(C$_1$-C$_2$) alkyl;
R$^2$ represents hydrogen and R$^3$ represents heterocyclyl; or R$^2$ and R$^3$ form, together with the carbon atom to which they are attached, a 5- to 7-membered saturated carbocyclic ring which is unsubstituted or mono- or di-substituted with fluoro; and
R$^4$ represents hydrogen or heteroaryl which is unsubstituted or mono- or di-substituted with (C$_1$-C$_4$)alkyl, (C$_1$-C$_3$)fluoroalkyl or halogen;
or a salt of such a compound.

2. The compound of formula (I) according to claim 1, wherein
n represents 1 or 2;
X represents —O— or —CH$_2$—;
R$^1$ represents hydrogen;
R$^2$ represents hydrogen and R$^3$ represents heterocyclyl; or R$^2$ and R$^3$ form, together with the carbon atom to which they are attached, a 6- or 7-membered saturated carbocyclic ring which is unsubstituted or mono- or di-substituted with fluoro; and
R$^4$ represents heteroaryl which is unsubstituted or mono- or di-substituted with (C$_1$-C$_4$)alkyl, (C$_1$-C$_3$)fluoroalkyl or halogen;
or a salt of such a compound.

3. The compound of formula (I) according to claim 1, wherein
n represents 1 or 2;
X represents —O— or —CH$_2$—;
IV represents hydrogen;
R$^2$ and R$^3$ form, together with the carbon atom to which they are attached, a 6-membered saturated carbocyclic ring which is unsubstituted or di-substituted with fluoro; and
R$^4$ represents a 6-membered heteroaryl group, which group is mono-substituted with chloro;
or a salt of such a compound.

4. The compound of formula (I) according to claim 1, wherein
X represents —O—;
or a salt of such a compound.

5. The compound of formula (I) according to claim 1, wherein
X represents —CH$_2$—;
or a salt of such a compound.

6. The compound of formula (I) according to claim 1, wherein
R$^2$ represents hydrogen and R$^3$ represents heterocyclyl;
or a salt of such a compound.

7. The compound of formula (I) according to claim 1, wherein
R$^2$ and R$^3$ form, together with the carbon atom to which they are attached, a 6-membered saturated carbocyclic ring which is unsubstituted or di-substituted with fluoro;
or a salt of such a compound.

8. The compound of formula (I) according to claim 1, wherein
R$^4$ represents a 6-membered heteroaryl group, which group is unsubstituted or mono-substituted with methyl, trifluoromethyl or chloro;
or a salt of such a compound.

9. The compound of formula (I) according to claim 1, selected from the group consisting of:
N-(1-cycloheptyl-2-hydroxyethyl)-5,6-dihydrofuro[2,3-d]thiazole-6-carboxamide;
N-((1-(6-chloropyridin-3-yl)cyclohexyl)methyl)-5,6-dihydrofuro[2,3-d]thiazole-6-carboxamide;
N-(2-(4,4-difluoropiperidin-1-yl)-2-(2-methylpyrimidin-5-yl)ethyl)-5,6-dihydrofuro[2,3-d]thiazole-6-carboxamide;
N-(2-morpholino-2-(6-(trifluoromethyl)pyridin-3-yl)ethyl)-5,6-dihydrofuro[2,3-d]thiazole-6-carboxamide;
N—((S)-1-cyclohexyl-2-hydroxyethyl)-5,6-dihydro-4H-cyclopenta[d]thiazole-6-carboxamide;
N-(2-(2-methylpyrimidin-5-yl)-2-morpholinoethyl)-5,6-dihydro-4H-cyclopenta[d]thiazole-6-carboxamide;
N-(2-(4,4-difluoropiperidin-1-yl)-2-(2-methylpyrimidin-5-yl)ethyl)-5,6-dihydro-4H-cyclopenta[d]thiazole-6-carboxamide;
N—((S)-1-cyclohexyl-2-hydroxyethyl)-6,7-dihydro-5H-pyrano[2,3-d]thiazole-7-carboxamide;
N-(2-(2-methylpyrimidin-5-yl)-2-morpholinoethyl)-6,7-dihydro-5H-pyrano[2,3-d]thiazole-7-carboxamide;
N-(2-(6-chloropyridin-3-yl)-2-(4,4-difluoropiperidin-1-yl)ethyl)-6,7-dihydro-5H-pyrano[2,3-d]thiazole-7-carboxamide;
N—((R)-1-cyclohexylethyl)-4,5,6,7-tetrahydrobenzo[d]thiazole-7-carboxamide;
N—((S)-1-cyclohexyl-2-hydroxyethyl)-4,5,6,7-tetrahydrobenzo[d]thiazole-7-carboxamide;
N-((1-(6-chloropyridin-3-yl)cyclohexyl)methyl)-4,5,6,7-tetrahydrobenzo[d]thiazole-7-carboxamide;
N-((1-(6-chloropyridin-3-yl)-4,4-difluorocyclohexyl)methyl)-4,5,6,7-tetrahydrobenzo[d]thiazole-7-carboxamide;
N-(2-morpholino-2-(2-(trifluoromethyl)pyrimidin-5-yl)ethyl)-4,5,6,7-tetrahydrobenzo[d]thiazole-7-carboxamide;
N—((S)-1-cyclohexyl-2-hydroxyethyl)-(S)-5,6,7,8-tetrahydro-4H-cyclohepta[d]thiazole-8-carboxamide; and
N—((S)-1-cyclohexyl-2-hydroxyethyl)-(R)-5,6,7,8-tetrahydro-4H-cyclohepta[d]thiazole-8-carboxamide;
or a salt of such a compound.

10. A pharmaceutical composition containing, as active principle, the compound of formula (I) according to claim 1, or a pharmaceutically acceptable salt thereof, and at least one therapeutically inert excipient.

11. A pharmaceutical composition containing, as active principle, a compound of formula (I) according to claim 9, or a pharmaceutically acceptable salt thereof, and at least one therapeutically inert excipient.

12. A method for the treatment of a disease selected from spinal cord injury, stroke, Alzheimer's disease, epilepsy, amyotrophic lateral sclerosis, pain, rheumatoid arthritis, asthma, chronic obstructive pulmonary disease, lung emphysema, glomerulonephritis, irritable bowel syndrome, psoriasis, atopic dermatitis, Crohn's disease, ulcerative colitis, diabetes mellitus, osteoporosis, and ischemic heart disease, comprising administering to a subject a pharmaceutically active amount of a compound of formula (I) according to claim 1 or a pharmaceutically acceptable salt thereof.

13. A method for the treatment of a disease selected from spinal cord injury, stroke, Alzheimer's disease, epilepsy, amyotrophic lateral sclerosis, pain, rheumatoid arthritis, asthma, chronic obstructive pulmonary disease, lung emphysema, glomerulonephritis, irritable bowel syndrome, psoriasis, atopic dermatitis, Crohn's disease, ulcerative colitis, diabetes mellitus, osteoporosis, and ischemic heart disease, comprising administering to a subject a pharmaceutically active amount of a compound of formula (I) according to claim 9 or a pharmaceutically acceptable salt thereof.

14. The compound of formula (I) according to claim 2, wherein $R^2$ represents hydrogen and $R^3$ represents heterocyclyl;

or a salt of such a compound.

15. The compound of formula (I) according to claim 2, wherein $R^2$ and $R^3$ form, together with the carbon atom to which they are attached, a 6-membered saturated carbocyclic ring which is unsubstituted or di-substituted with fluoro;

or a salt of such a compound.

16. The compound of formula (I) according to claim 2, wherein $R^4$ represents a 6-membered heteroaryl group, which group is unsubstituted or mono-substituted with methyl, trifluoromethyl or chloro;

or a salt of such a compound.

17. The method of claim 12, wherein the disease is selected from spinal cord injury, Alzheimer's disease, amyotrophic lateral sclerosis, pain, rheumatoid arthritis, asthma, chronic obstructive pulmonary disease, lung emphysema, glomerulonephritis, irritable bowel syndrome, psoriasis, atopic dermatitis, Crohn's disease, ulcerative colitis, diabetes mellitus, and osteoporosis.

* * * * *

```
                        SEQUENCE LISTING

<160> NUMBER OF SEQ ID NOS: 2

<210> SEQ ID NO 1
<211> LENGTH: 35
<212> TYPE: DNA
<213> ORGANISM: Homo sapiens
<220> FEATURE:
<221> NAME/KEY: source
<222> LOCATION: 1..35
<223> OTHER INFORMATION: /mol_type="DNA"
      /organism="Homo sapiens"

<400> SEQUENCE: 1
atcgcggccg ctcagtaagg actcttgaag ccact                              35

<210> SEQ ID NO 2
<211> LENGTH: 38
<212> TYPE: DNA
<213> ORGANISM: Homo sapiens
<220> FEATURE:
<221> NAME/KEY: source
<222> LOCATION: 1..38
<223> OTHER INFORMATION: /mol_type="DNA"
      /organism="Homo sapiens"

<400> SEQUENCE: 2
cgccgctagc accaccatgc cggcctgctg cagctgca                           38
```